(12) United States Patent
Takekoshi et al.

(10) Patent No.: US 10,888,298 B2
(45) Date of Patent: Jan. 12, 2021

(54) RADIOGRAPHIC IMAGING SYSTEM, MEDICAL IMAGE CAPTURING SYSTEM, MEDICAL IMAGE CAPTURING METHOD, AND STORAGE MEDIUM

(71) Applicant: CANON KABUSHIKI KAISHA, Tokyo (JP)

(72) Inventors: Koji Takekoshi, Fujisawa (JP); Hironori Yamashita, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/254,418

(22) Filed: Jan. 22, 2019

(65) Prior Publication Data
US 2019/0231297 A1  Aug. 1, 2019

(30) Foreign Application Priority Data
Jan. 26, 2018  (JP) ................................ 2018-011775

(51) Int. Cl.
*A61B 6/00* (2006.01)
*G16H 40/60* (2018.01)
*A61B 6/10* (2006.01)

(52) U.S. Cl.
CPC .............. *A61B 6/548* (2013.01); *A61B 6/467* (2013.01); *A61B 6/54* (2013.01); *G16H 40/60* (2018.01); *A61B 6/10* (2013.01); *A61B 6/563* (2013.01)

(58) Field of Classification Search
CPC .................................. A61B 6/548; A61B 6/54
See application file for complete search history.

(56) References Cited

U.S. PATENT DOCUMENTS

| | | |
|---|---|---|
| 2006/0165371 A1 | 7/2006 | Zwart |
| 2011/0306882 A1 | 12/2011 | Hannon |
| 2013/0321284 A1 | 12/2013 | Bello |
| 2014/0275954 A1 | 9/2014 | Ohta |
| 2016/0022231 A1 | 1/2016 | Nonaka |
| 2016/0228087 A1* | 8/2016 | Oda et al. |
| 2017/0318362 A1 | 11/2017 | Mu |
| 2017/0360390 A1 | 12/2017 | Tajima |

FOREIGN PATENT DOCUMENTS

| | | |
|---|---|---|
| JP | S57-193851 A | 11/1982 |
| JP | H09-248295 A | 9/1997 |
| JP | 2005-266947 A | 9/2005 |

(Continued)

*Primary Examiner* — Yara B Green
(74) *Attorney, Agent, or Firm* — Canon U.S.A., Inc. I.P. Division

(57) ABSTRACT

A radiographic imaging system, a radiographic imaging method, and a storage medium are capable of avoiding the collision of the operations, even if the operations based on a plurality of terminal apparatuses occur. The radiographic imaging system includes a radiographic imaging apparatus configured to generate a radiographic image based on radiation emitted from a radiation generating apparatus, and a control unit configured to control the radiographic imaging apparatus based on instructions from a first terminal apparatus and a second terminal apparatus. The second terminal apparatus acquires a right to control the control unit from the first terminal apparatus, and the control unit controls the radiographic imaging apparatus based on an instruction from the second terminal apparatus.

15 Claims, 15 Drawing Sheets

(56) References Cited

FOREIGN PATENT DOCUMENTS

| | | | |
|---|---|---|---|
| JP | 2006-065850 | A | 3/2006 |
| JP | 2006-247137 | A | 9/2006 |
| JP | 2008-204292 | A | 9/2008 |
| JP | 2009-268586 | A | 11/2009 |
| JP | 2011-114869 | A | 6/2011 |
| JP | 2012-227603 | A | 11/2012 |
| JP | 2014-211764 | A | 11/2014 |
| JP | 2016-147044 | A | 8/2016 |
| JP | 6195348 | B2 | 9/2017 |

* cited by examiner

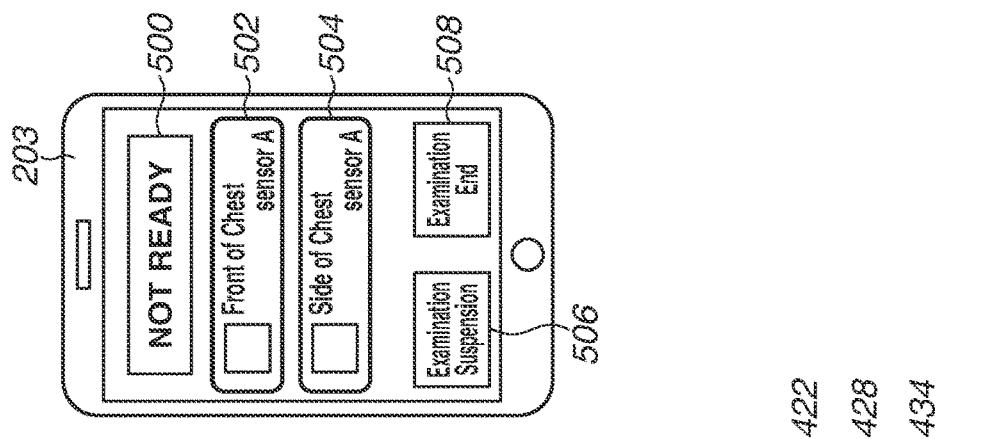
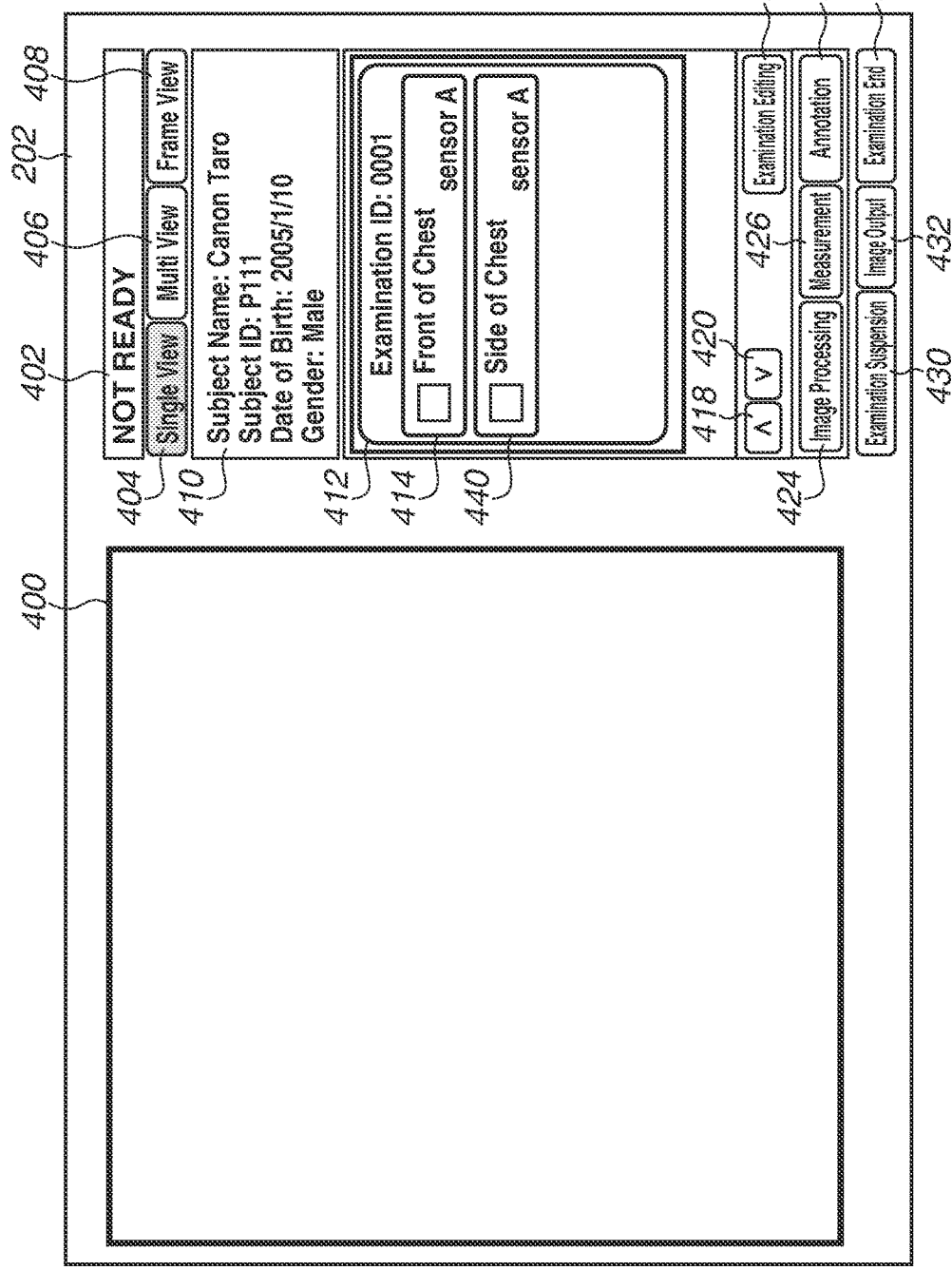
FIG. 10A
FIG. 10B

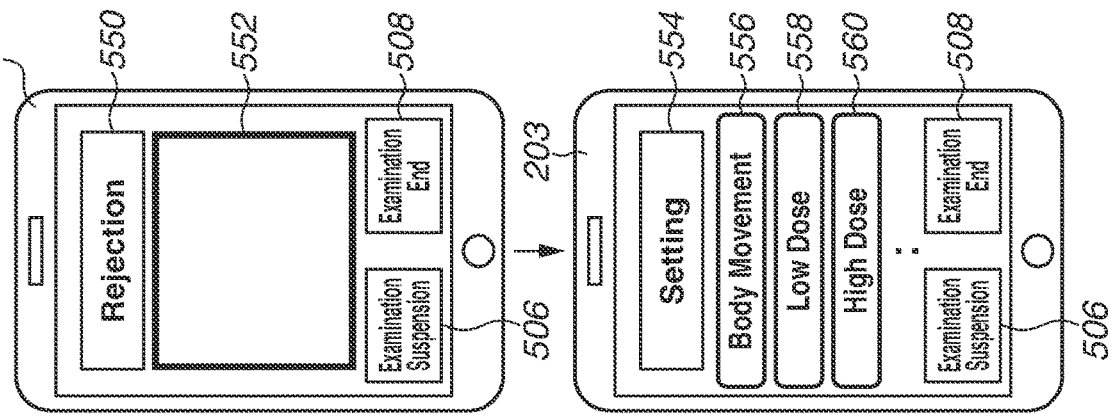
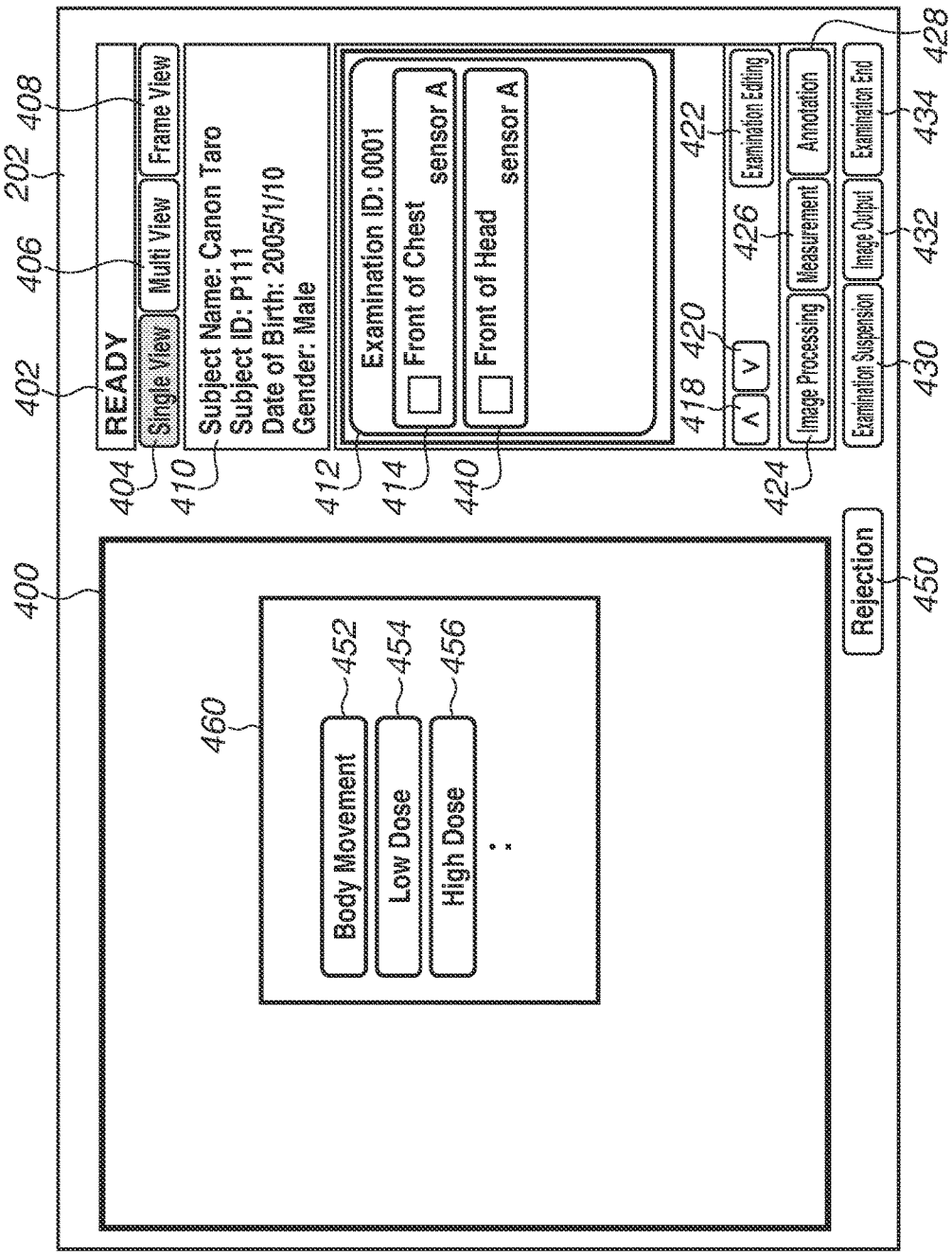
FIG. 12A
FIG. 12B

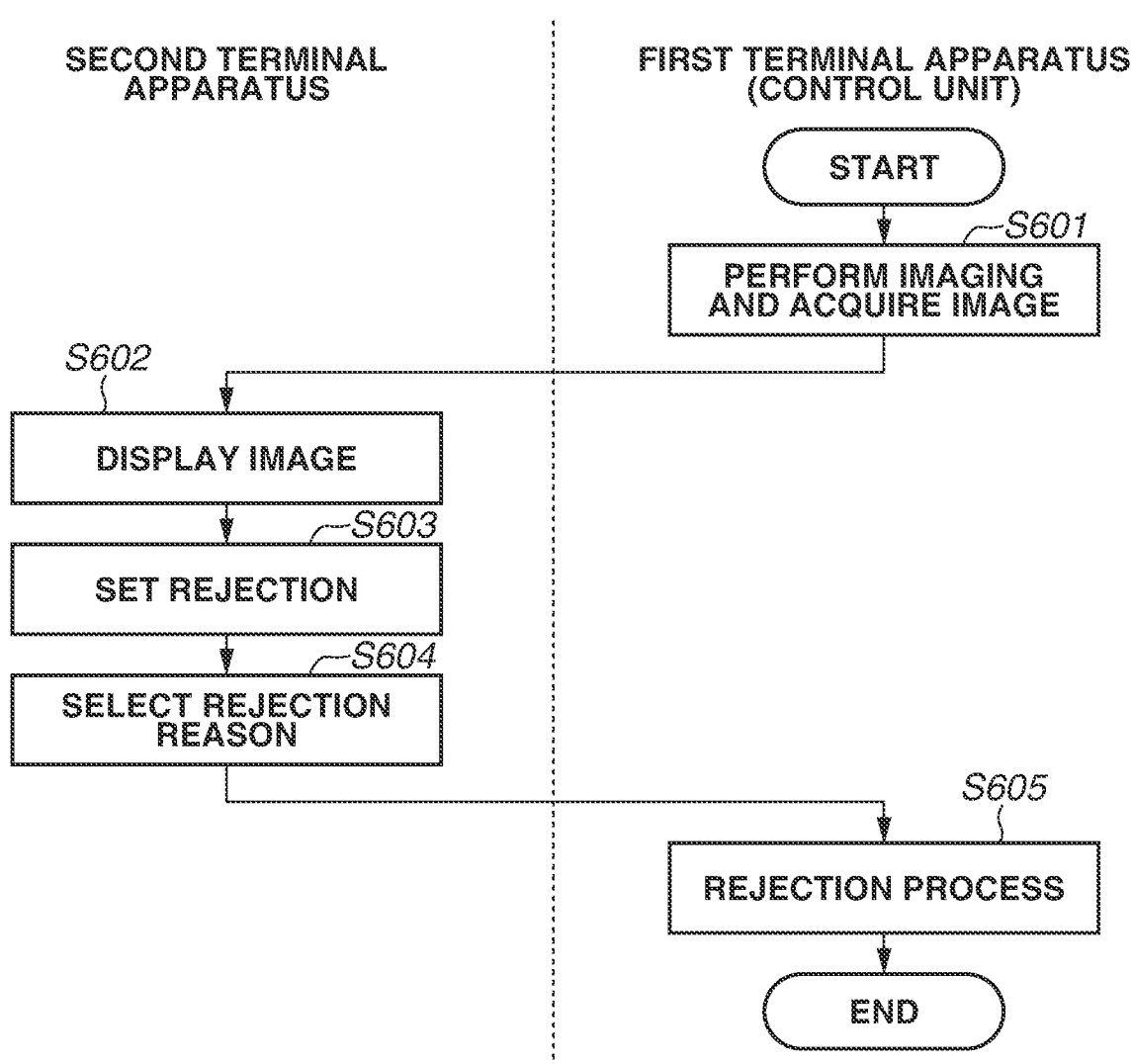

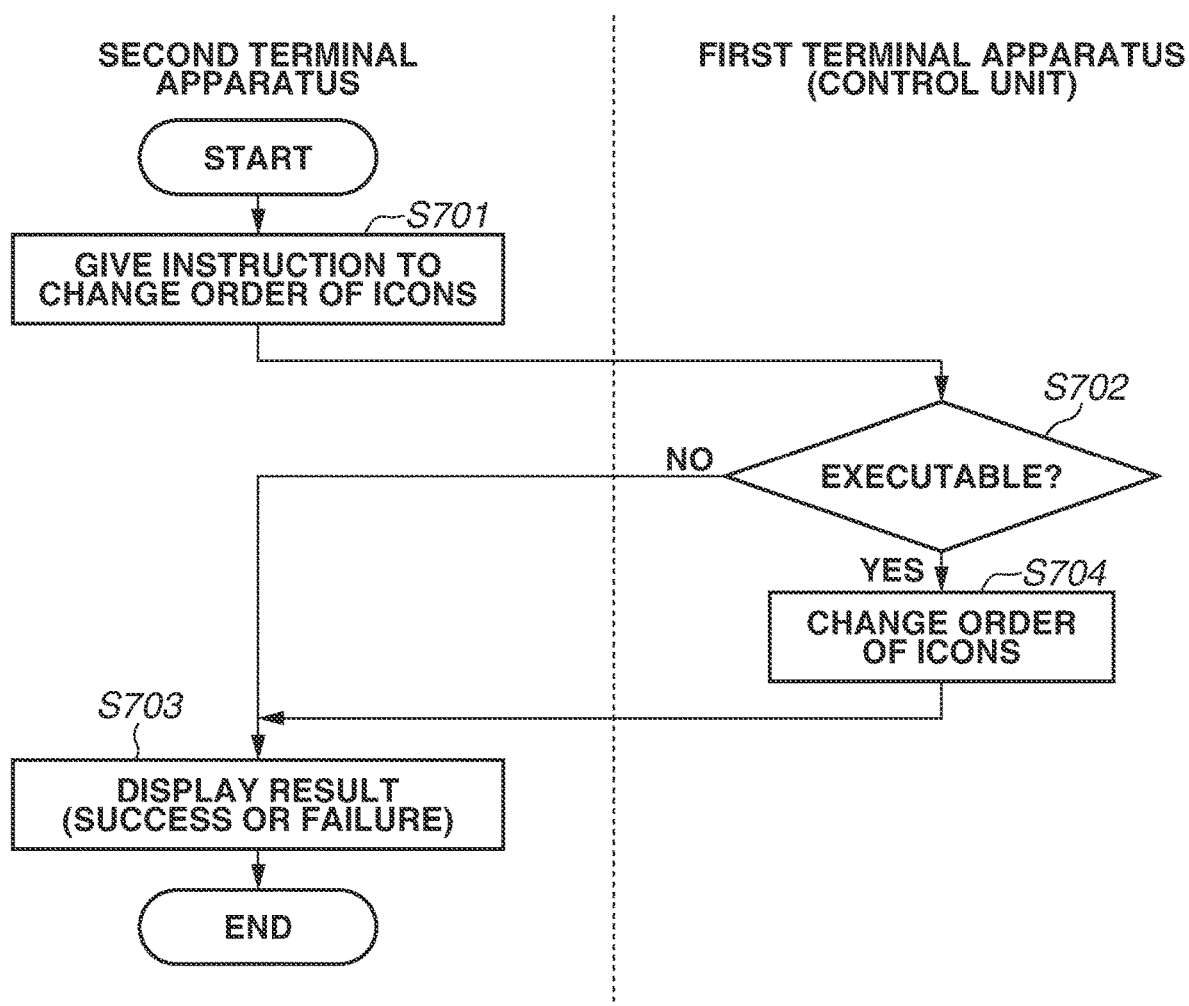

RADIOGRAPHIC IMAGING SYSTEM, MEDICAL IMAGE CAPTURING SYSTEM, MEDICAL IMAGE CAPTURING METHOD, AND STORAGE MEDIUM

BACKGROUND OF THE INVENTION

Field of the Invention

The present invention relates to a radiographic imaging system and a medical image capturing system for performing radiographic imaging, and in particular, relates to the control of radiographic imaging.

Description of the Related Art

In recent years, in a radiographic imaging system, a radiographic image based on radiation emitted to a radiographic imaging apparatus is generated, and an image can be confirmed immediately after radiographic imaging is performed. Further, due to the advancement of network cooperation technology, different apparatuses can operate cooperatively with each other.

For example, the publication of Japanese Patent No. 6195348 discusses a medical system for performing control according to operation instructions input via a plurality of terminal apparatuses. The medical system processes operation instructions by giving priority to each operation based on a person who performs the operation, a role, and a place.

In the medical system discussed in the publication of Japanese Patent No. 6195348, however, the priority is determined in advance. For this reason, in a case where an operation that unexpectedly needs to be processed occurs, an operation having high priority collides with the operation that unexpectedly needs to be processed.

SUMMARY OF THE INVENTION

The present invention is directed to a radiographic imaging system, a radiographic imaging method, and a storage medium capable of avoiding the collision of the operations, even if the operations based on a plurality of terminal apparatuses occur. According to an aspect of the present invention, a radiographic imaging system includes a radiographic imaging apparatus configured to generate a radiographic image based on radiation emitted from a radiation generating apparatus, and a control unit configured to control the radiographic imaging apparatus based on instructions from a first terminal apparatus and a second terminal apparatus, the second terminal apparatus acquires a right to control the control unit from the first terminal apparatus, and the control unit controls the radiographic imaging apparatus based on an instruction from the second terminal apparatus.

Further features of the present invention will become apparent from the following description of exemplary embodiments with reference to the attached drawings.

BRIEF DESCRIPTION OF THE DRAWINGS

FIGS. 10A and 10B are diagrams illustrating screens of the radiographic imaging system according to the third exemplary embodiment.

FIGS. 12A and 12B are diagrams illustrating screens of a radiographic imaging system according to a fourth exemplary embodiment.

FIG. 13 is a flowchart illustrating an operation form of the radiographic imaging system according to the fourth exemplary embodiment.

FIG. 15 is a flowchart illustrating an operation form of the radiographic imaging system according to the fifth exemplary embodiment.

DESCRIPTION OF THE EMBODIMENTS

With reference to the attached drawings, suitable exemplary embodiments f the present invention will be described below.

Figure 1:
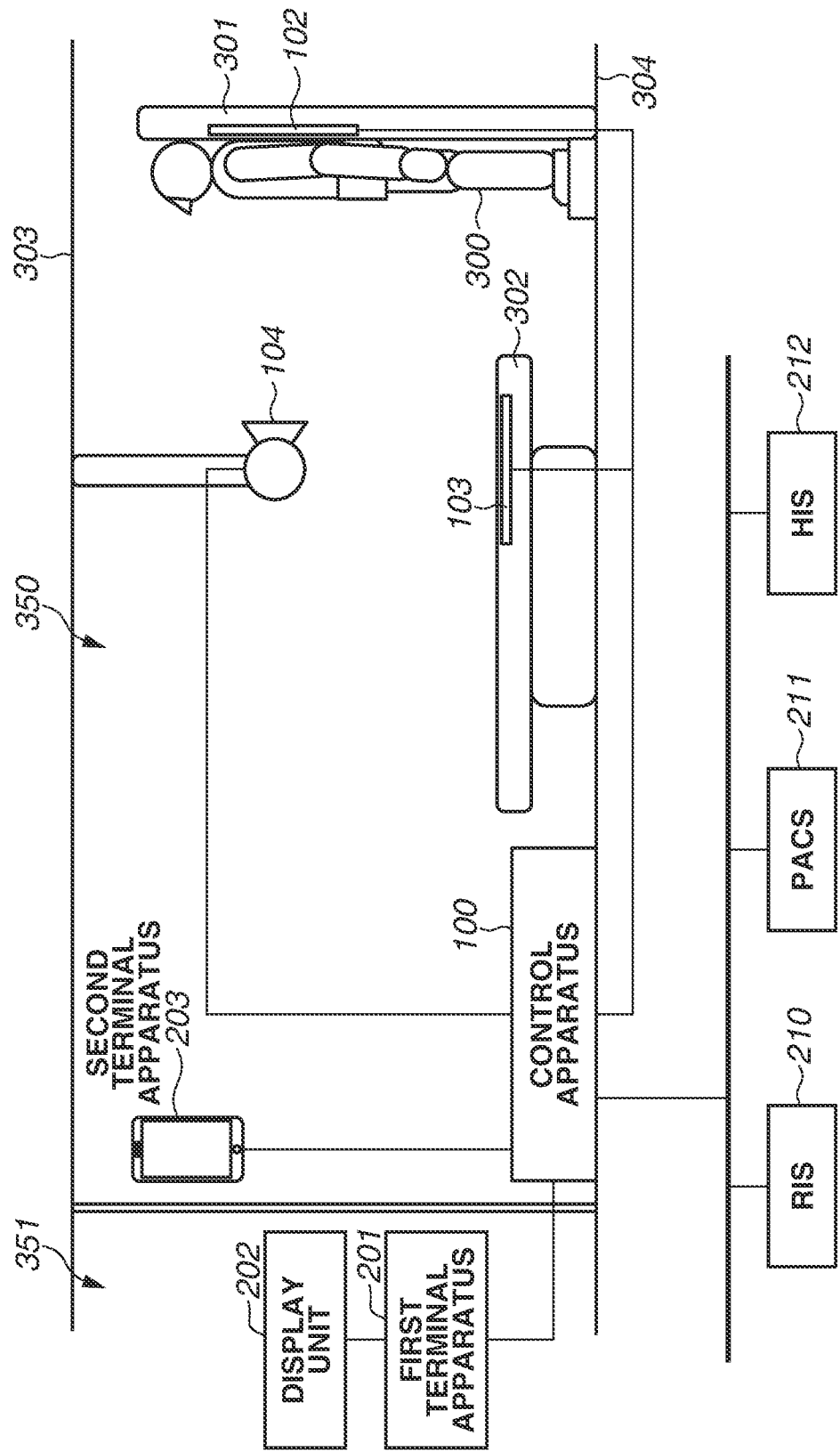
FIG. 1 is a diagram illustrating a configuration of a radiographic imaging system.

A first exemplary embodiment is described. FIG. 1 is a diagram illustrating the configuration of a radiographic imaging system, which is a type of a medical image capturing system according to the present invention. The radiographic imaging system includes radiographic imaging apparatuses 102 and 103, a radiation generating apparatus 104 that generates radiation, and a control apparatus 100 that controls the radiographic imaging apparatuses 102 and 103 and the radiation generating apparatus 104, thereby performing imaging control.

The radiation generating apparatus 104 is installed movably relative to a ceiling 303. The radiographic imaging system is a ceiling running system. The radiation generating apparatus 104 can move three-dimensionally, namely upward, downward, leftward, and rightward, relative to the ceiling 303. A stand 301 is installed and fixed to a floor surface 304. The stand 301 is a support base for upright imaging. A bed 302 is installed and fixed to the floor surface 304. The bed 302 is a support base for recumbent imaging. In the stand 301 and the bed 302, the radiographic imaging apparatuses 102 and 103, respectively, are installed. The radiographic imaging apparatuses 102 and 103 may be installed by replacing the radiographic imaging apparatuses 102 and 103 with each other. That is, the radiographic imaging apparatus 102 may be installed in the bed 302, and the radiographic imaging apparatus 103 may be installed in the stand 301.

The radiographic imaging system includes a first terminal apparatus 201 (e.g., an operation console) with which an operator inputs an instruction to the control apparatus 100, and a display unit 202 that displays a captured radiographic image and various types of information. Further, the radiographic imaging system includes a second terminal apparatus 203 (e.g., a mobile terminal) with which the operator inputs an instruction to the control apparatus 100 and which displays a captured radiographic image and various types of information. The first terminal apparatus 201 and the second terminal apparatus 203 include a mouse, a keyboard, and a touch panel and can notify the control apparatus 100 of an instruction from the operator. The first terminal apparatus 201 and the display unit 202 are installed in a place 351 outside an imaging room (an operation room). The second terminal apparatus 203 is installed in an imaging room 350. The second terminal apparatus 203 only needs to include an operation unit and a display unit, and may not be a mobile terminal.

The control apparatus 100 communicates with the radiographic imaging apparatus 102 or 103 and controls radiographic imaging. Further, the control apparatus 100 communicates with the radiation generating apparatus 104 and controls the radiation generating apparatus 104 to emit radiation. Although in the present exemplary embodiment, a description is given of a form in which two radiographic imaging apparatuses are provided, the number of radiographic imaging apparatuses is not limited to two. Alternatively, a single radiographic imaging apparatus may be provided, or three or more radiographic imaging apparatuses may be provided.

Under control of the control apparatus 100, the states of the radiographic imaging apparatuses 102 and 103 each transition to the state where the radiographic imaging apparatus can perform imaging (a ready state). Then, the radiographic imaging apparatus performs radiographic imaging in synchronization with the control apparatus 100. The radiographic imaging apparatuses 102 and 103 can each capture radiation emitted from the radiation generating apparatus 104 and generate a radiographic image.

Specifically, the radiographic imaging apparatuses 102 and 103 each detect radiation transmitted through a subject as an electric charge corresponding to the amount of transmitted radiation. For example, for each of the radiographic imaging apparatuses 102 and 103, a direct conversion sensor that directly converts radiation such as a-Se into an electric charge, or an indirect sensor that uses a scintillator such as CsI and a photoelectric conversion element such as a-Si is used. Further, the radiographic imaging apparatuses 102 and 103 each perform analog-to-digital (A/D) conversion on the detected electric charge to generate a radiographic image, and output the generated radiographic image to the control apparatus 100.

The control apparatus 100 can acquire the radiographic images generated by the radiographic imaging apparatuses 102 and 103. Each of the radiographic images generated by the radiographic imaging apparatuses 102 and 103 is displayed on the display unit 202 of the first terminal apparatus 201 or displayed on the display unit of the second terminal apparatus 203 via the control apparatus 100. The control apparatus 100 has the function of performing various types of image processing such as a noise removal process and a gradation process on the radiographic image.

Further, the control apparatus 100 can also set an imaging condition for the radiation generating apparatus 104 or cause the radiation generating apparatus 101 to emit radiation based on the set imaging condition.

As illustrated in FIG. 1, in the ceiling running system for the radiation generating apparatus 104, the position of the radiation generating apparatus 104 and the emission direction of the radiation generating apparatus 104 in the imaging room 350 are managed. As illustrated in FIG. 1, if the emission direction of the radiation generating apparatus 104 is the horizontal direction, radiation is emitted to the stand 301. In this way, the imaging orientation can be regarded as an upright position.

The control apparatus 100 is connected via a network to a radiology information system (RIS) 210 that notifies the control apparatus 100 of an examination order, a picture archiving and communication system (PACS) 211 that manages a radiographic image, and a hospital information system (HIS) 212 that manages the progress of an examination.

In the radiology department of a hospital, if the RIS 210 receives an examination order, the radiology department notifies the control apparatus 100 of imaging information (an imaging condition and an imaging procedure) regarding radiographic According to the received examination order, the control apparatus 100 executes radiographic imaging. Then, the control apparatus 100 assigns supplementary information including the examination order to a captured radiographic image and outputs the captured radiographic image and the supplementary information.

The PACS 211 is a server mainly for the purpose of managing an image. The PACS 211 includes a storage device that stores a radiographic image and supplementary information. Using a high-definition monitor connected to the PACS 211, examination work for examining a radiographic image, detailed post-processing, and diagnosis work are executed. As described above, the PACS 211 is notified of a radiographic image output from the control apparatus 100.

The HIS 212 is a hospital management system and includes a server that manages accounting information. To perform radiographic imaging, the operator inputs an examination instruction through a terminal of the HIS 212. Then, the HIS 212 notifies the radiology department of the hospital, which is a request destination, of the examination instruction. This request information is referred to as an "examination order". The examination order includes the department name of a request source, examination items, and personal data of a subject. The HIS 212 is notified of execution information about an examination in the radiographic imaging system. The execution information of which the HIS 212 is notified is also used for an accounting process after the examination in addition to the progress management of the examination.

The control apparatus 100, the MS 210, the PACS 211, and the HIS 212 are connected together via a network composed of, for example, a local area network (LAN) or a wide area network (WAN).

Next, a description is given of how the radiographic imaging system proceeds with an examination. First, the operator is notified of an examination order via the control apparatus 100. The examination order is displayed on the display unit 202 of the first terminal apparatus 201 or displayed on the display unit of the second terminal apparatus 203. The examination order is imported into the control apparatus 100, and subject information and an imaging content are identified. When the examination order reaches the operator, generally, a subject has been waiting for being imaged in the place 351 outside the imaging room. The operator calls the subject into the imaging room 350 according to the examination order and prepares for an examination. When the operator calls the subject into the imaging room 350, the operator confirms the name and the date of birth of the subject to avoid mixing up subjects. At this time, the operator confirms a subject name for which the examination order is received, as the subject information on a display (not illustrated) in the imaging room 350, or confirms the subject name with the second terminal apparatus 203. If imaging is prepared, then according to the examination order indicating imaging at a recumbent position and imaging at an upright position, the operator adjusts the positions of the radiation generating apparatus 104, the subject, and the radiographic imaging apparatuses 102 and 103. Depending on the state of the subject or the content of the examination order, the operator may make a change, such as changing the imaging order or replacing the upright position and the recumbent position, based on the determination of the operator. Then, the operator moves from the imaging room 350 to the place 351 outside the imaging room, where the first terminal apparatus 201 is provided. If the operator determines that radiographic imaging can be performed, the operator emits radiation and captures a radiographic image. Normally, the captured radiographic image is displayed on the display unit 202 in the place 351 outside the imaging room. Accordingly, if the operator confirms the radiographic image and there is no problem, the operator moves to the imaging room 350 to perform positioning for next imaging. If next imaging is not to be performed, the examination ends. Then, the subject leaves the imaging room 350.

Figure 2:
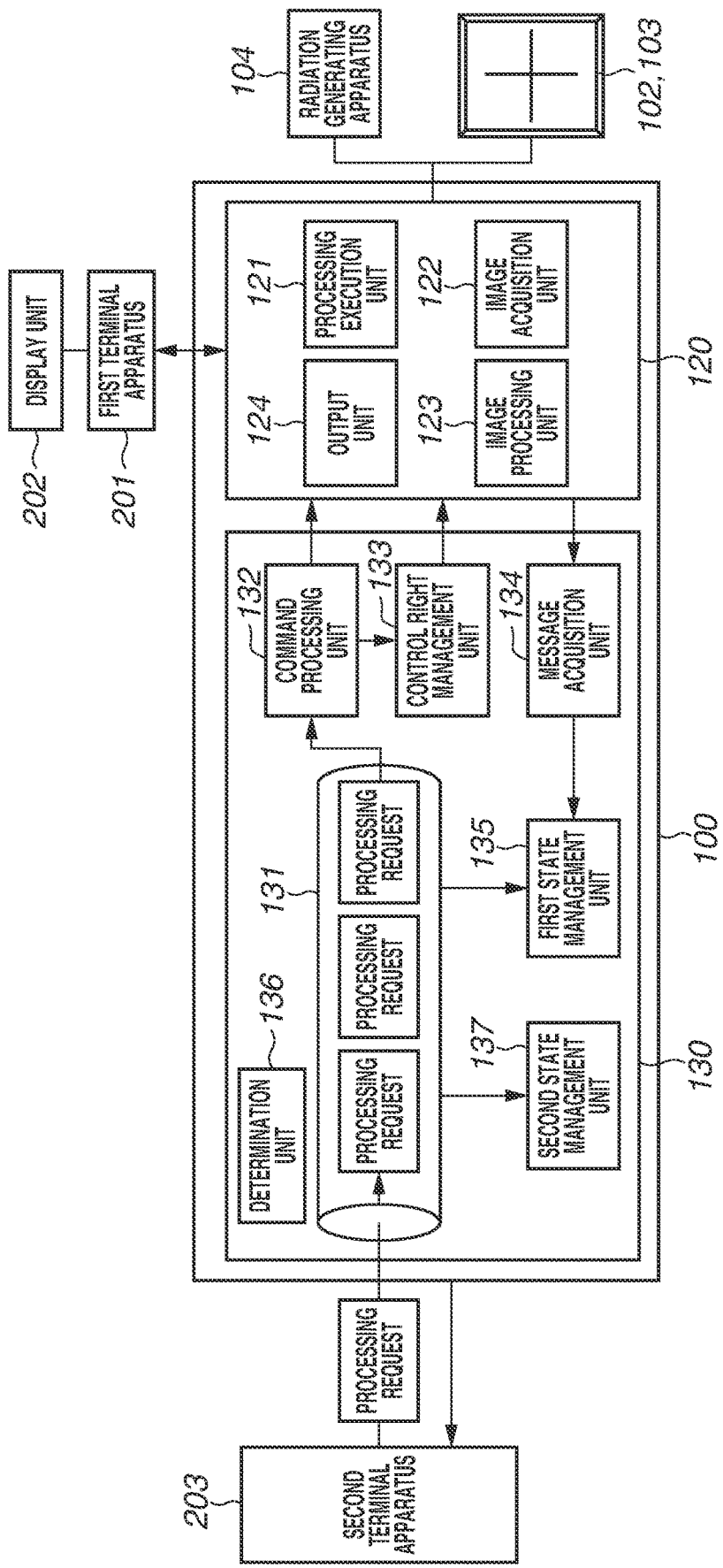
FIG. 2 is a diagram illustrating a configuration of a control apparatus of the radiographic imaging system.

Next, with reference to FIG. 2, the control apparatus 100 of the radiographic imaging system is described. The control apparatus 100 mainly includes a control unit 120 that receives processing requests from the first terminal apparatus 201 and the second terminal apparatus 203 and performs control, and an extended control unit 130 that manages a processing request from the second terminal apparatus 203 and performs control. Although in the present exemplary embodiment, the control unit 120 and the extended control unit 130 are separately configured, the control unit 120 and the extended control unit 130 may function as a single control unit.

The control apparatus 100 is connected to the radiographic imaging apparatuses 102 and 103. Specifically, the control apparatus 100 is connected to the radiographic imaging apparatuses 102 and 103 via a wired or wireless network or a dedicated line. The radiographic imaging apparatuses 102 and 103 each capture radiation emitted from the radiation generating apparatus 104 and output a radiographic image to the control apparatus 100. The control apparatus 100 has an application function that operates on a computer. The control apparatus 100 controls the operations of the radiographic imaging apparatuses 102 and 103 and also outputs a radiographic image or a graphical user interface (GUI) to the first terminal apparatus 201 or the second terminal apparatus 203. The control apparatus 100 has the function of performing image processing such as a noise removal process, a gradation process, and an emphasis process on each of the radiographic images output from the radiographic imaging apparatuses 102 and 103. Further, the control apparatus 100 can also perform image processing such as cropping and rotation on each of the radiographic images output from the radiographic imaging apparatuses 102 and 103.

The control unit 120 of the control apparatus 100 includes a processing execution unit 121 that causes the components of the radiographic imaging apparatuses 102 and 103 to execute processing. The processing execution unit 121 is a unit that, based on a processing request from the first terminal apparatus 201 or the second terminal apparatus 203, controls the radiation generating apparatus 104 and the radiographic imaging apparatuses 102 and 103.

The control unit 120 includes an image acquisition unit 122 that acquires a radiographic image (image data) output from each of the radiographic imaging apparatuses 102 and 103, an image processing unit 123 that performs image processing on the radiographic image acquired by the image acquisition unit 122, and an output unit 124 that outputs the radiographic image to an external apparatus (the PACS 211). The control unit 120 is configured such that a computer executes various types of processing according to a program stored in a memory (a read-only memory (ROM) or a random-access memory (RAM)).

The extended control unit 130 is a Dynamic-link library (DLL) that operates as a plug-in for the control unit 120. With a plug-in structure, the extended control unit 130 can also operate alone. Although the control unit 120 and the extended control unit 130 can also operate cooperatively with each other, a plug-in structure does not necessarily need to be used. The control unit 120 and the extended control unit 130 may be configured to always operate cooperatively with each other. A description is given here on the assumption that the extended control unit 130 is a DLL having a plug-in structure.

The extended control unit 130 performs processing that is broadly divided into two types of processing, namely processing based on a processing request from the second terminal apparatus 203 and processing on the control unit 120. The extended control unit 130 includes a processing request management unit 131 that manages processing requests from the second terminal apparatus 203. The processing request management unit 131 manages the processing requests using a first-in-first-out (FIFO) structure. The processing request management unit 131 has a data structure based on a so-called queue, and processing requests input from the second terminal apparatus 203 to the processing request management unit 131 are taken out in the order of input.

In this case, the input of a processing request to the processing request management unit 131 is referred to as "enqueue", and the taking out of a processing request from the processing request management unit 131 is referred to as "dequeue", Further, a processing request from the second terminal apparatus 203 is referred to as a "command", and a notification from the control unit 120 is referred to as a "message".

The extended control unit 130 includes a command processing unit 132 that notifies the control unit 120 of a processing request dequeued from the processing request management unit 131 as a command. The extended control unit 130 includes a control right management unit 133 that manages a control right in the first terminal apparatus 201 and the second terminal apparatus 203 based on a command as a processing request regarding the control right. The extended control unit 130 includes a message acquisition unit 134 that acquires a message indicating that particular control is performed by the control unit 120. Further, the extended control unit 130 includes a first state management unit 135 that manages the state of the control unit 120 based on a message acquired by the message acquisition unit 134, and a second state management unit 137 that manages the state of the control unit 120 after a dequeued processing request is executed, i.e., after a queue process is performed. The first state management unit 135 manages the current state of the control unit 120, and the second state management unit 137 manages the future state of the control unit 120 after processing is performed according to a processing request.

The processing on a message acquired by the message acquisition unit 134 is described. When the state of the control unit 120 changes as a result of the control unit 120 causing the processing execution unit 121 to perform processing according to some processing request, the control unit 120 notifies the message acquisition unit 134 of a message that the state changes. If the message acquisition unit 134 receives a message from the control unit 120 and the state of the control unit 120 changes, the message acquisition unit 134 changes the state of the control unit 120 managed by the first state management unit 135.

Figure 3:
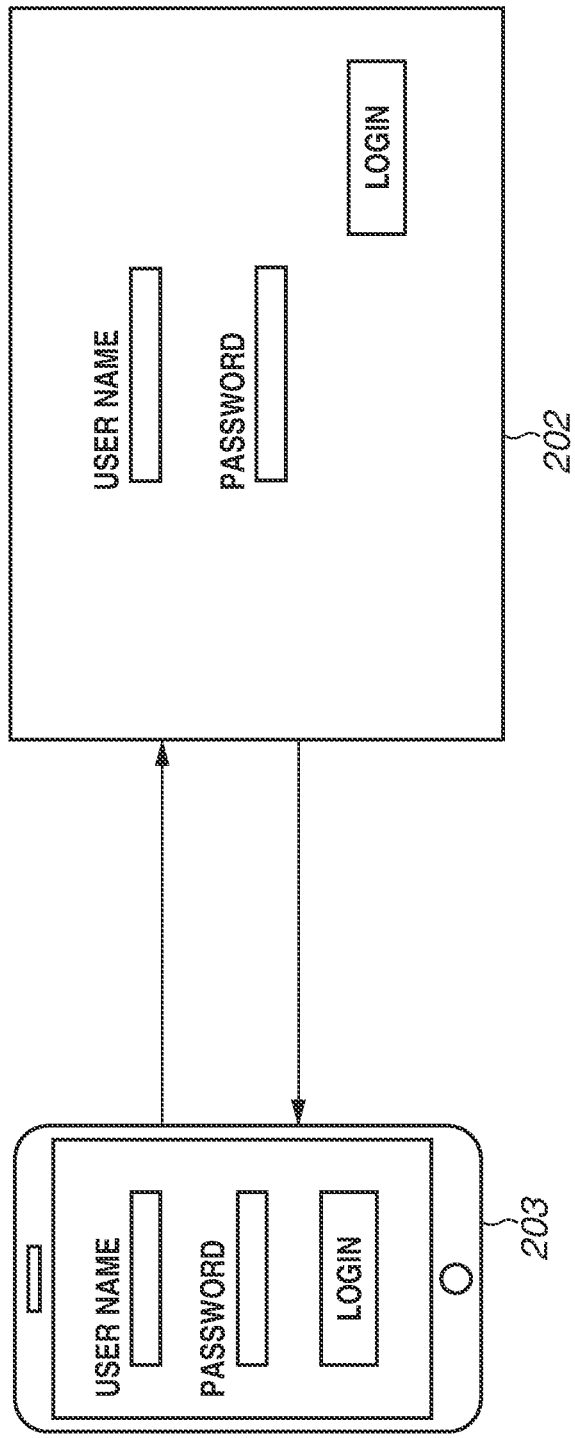
FIGS. 3A and 3B are diagrams illustrating a login operation for logging into the radiographic imaging system.

With reference to FIGS. 3A and 3B, a login operation for logging into the radiographic imaging system is described as a specific example of the processing of a message. This description is merely an example, and does not limit the present invention. The operator is carrying the second terminal apparatus 203. The second terminal apparatus 203 displays various types of information. Similarly, the first terminal apparatus 201 displays various types of information on the display unit 202. As illustrated in FIGS. 3A and 3B, the second terminal apparatus 203 and the display unit 202 each display a login screen. FIG. 3A is the display form of the display unit of the second terminal apparatus 203. FIG. 3B is the display form of the display unit 202 of the first terminal apparatus 201.

When the display unit 202 of the first terminal apparatus 201 displays the login screen, the control unit 120 of the control apparatus 100 notifies the second terminal apparatus 203 of a message that the login screen is displayed. Based on the content of the message, the second terminal apparatus 203 can recognize that the control unit 120 is in the state of waiting for a login. Then, the second terminal apparatus 203 displays the login screen. The operator may log in using the first terminal apparatus 201 or log in using the second terminal apparatus 203. If the operator logs in using the first terminal apparatus 201, a login process is performed, and according to the success or failure of the login process, the first terminal apparatus 201 operates according to the specifications. At this time, the second terminal apparatus 203 is notified of the result of the success or failure of the login process as a message. Accordingly, the second terminal apparatus 203 can also display a screen corresponding to the result of the login process.

If the operator logs in using the second terminal apparatus 203, the control unit 120 is notified of a command including information about a user name and a password and information indicating that a login operation is performed. Similarly to an operation on the first terminal apparatus 201, the control unit 120 sets the user name and the password in text boxes and performs a series of processes until a login process is performed. The control unit 120 notifies the second terminal apparatus 203 of the result of the success or failure of the login process, using a message. The second terminal apparatus 203 can display a screen corresponding to the content of the success or failure indicated by the message.

Then, based on instructions from the first terminal apparatus 201 and the second terminal apparatus 203, the control unit 120 controls the radiographic imaging apparatuses 102 and 103. At this time, the second terminal apparatus 203 acquires the right to control the control unit 120 from the first terminal apparatus 201, and based on a processing request from the second terminal apparatus 203, the control unit 120 controls the radiographic imaging apparatuses 102 and 103. The control right can also be said to be an exclusive right that cannot be controlled by another terminal apparatus. For example, when the second terminal apparatus 203 has the right to control the control unit 120, the first terminal apparatus 201 cannot control the control unit 120. When the first terminal apparatus 201 has the right to control the control unit 120, the second terminal apparatus 203 cannot control the control unit 120.

Figure 4:
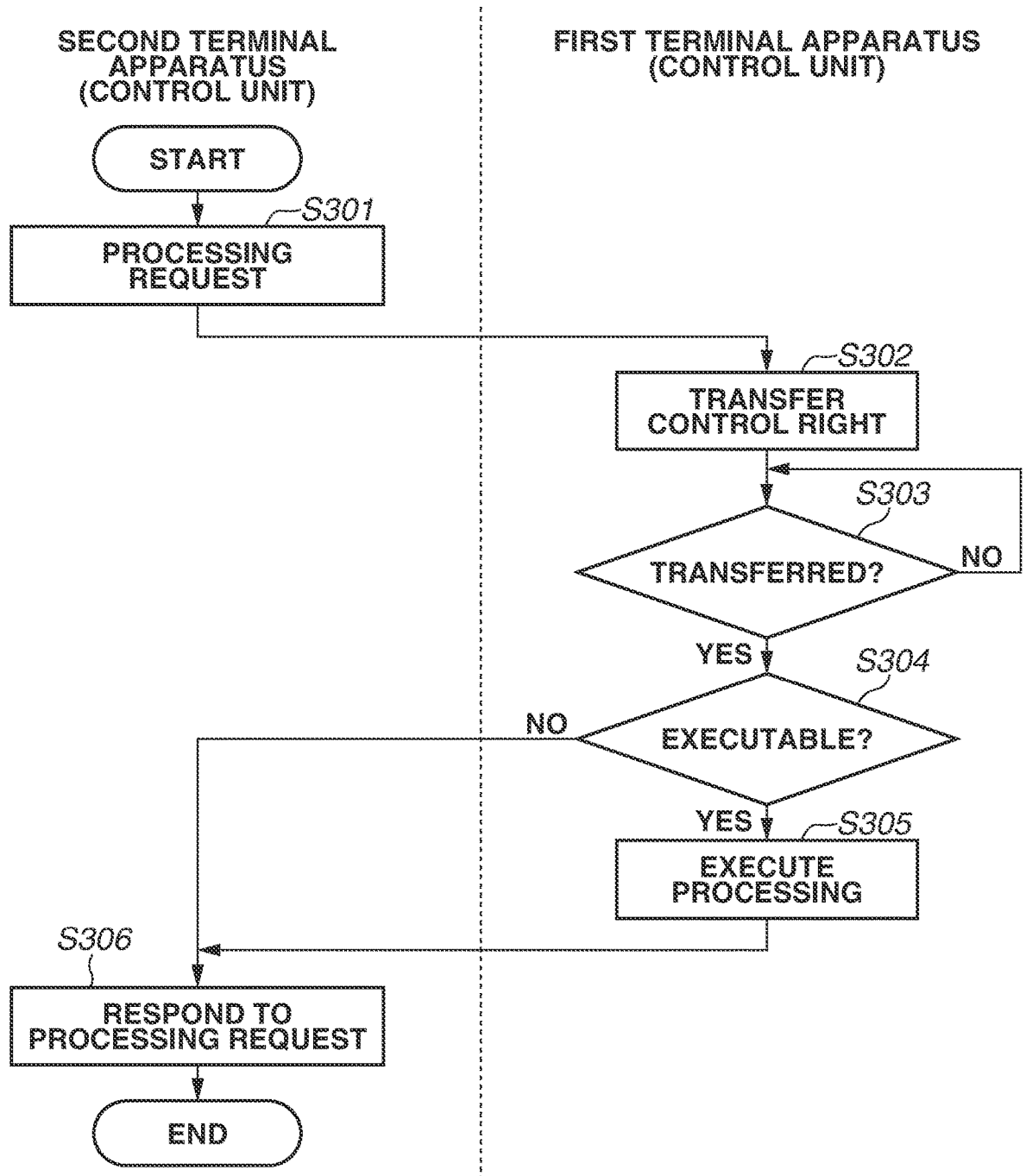
FIG. 4 is a flowchart illustrating an operation form of a radiographic imaging system according to a first exemplary embodiment.

With reference to a flowchart in FIG. 4, an operation form of the radiographic imaging system according to the first exemplary embodiment is described. The left side of FIG. 4 illustrates the operation of the second terminal apparatus 203 (the control unit 120), and the right side of FIG. 4 illustrates the operation of the first terminal apparatus 201 (the control unit 120).

In step S301, the second terminal apparatus 203 outputs a particular processing request. The control apparatus 100 is notified of the processing request. A command in the extended control unit 130 of the control apparatus 100 is converted into an application programming interface (API) so that the second terminal apparatus 203 can be notified of the command by calling the API.

In step S302, before the particular processing request from the second terminal apparatus 203 is processed, the right to control the control unit 120 owned by the first terminal apparatus 201 is transferred to the second terminal apparatus 203. That is, if a processing request is output from the second terminal apparatus 203, the right to control the control unit 120 owned by the first terminal apparatus 201 is transferred to the second terminal apparatus 203. The right to control the control unit 120 is transferred by acquiring a main thread or a GUT thread of the control unit 120 using an exclusive process such as mutex or a semaphore.

In step S303, if the transfer of the right to control the control unit 120 is successful in step S302 (Yes in step S303), the processing proceeds to step S304. If the transfer of the right to control the control unit 120 has failed (No in step S303), the second terminal apparatus 203 waits until the right to control the control unit 120 owned by the first terminal apparatus 201 is released. Alternatively, if the transfer of the right to control the control unit 120 has failed (No in step S303), it may be determined that a command process regarding the transfer of the control right is failed, and the processing may proceed to step S306.

In step S304, a determination unit 136 determines whether a command regarding the particular processing request can be executed. The first state management unit 135 manages the state of the control unit 120. The state of the control unit 120 is the current state of the control unit 120. The state of the control unit 120 is, for example, the state of a screen displayed on the display unit 202 via the first terminal apparatus 201, or the state of whether an operation icon on the screen can be operated. For example, if the display unit 202 is in the display state illustrated in FIG. 3B, the state of the screen is the login screen, and a login icon is in the state where the login icon can be operated. Meanwhile, since a screen other than the login screen is not displayed, normally, the determination unit 136 can determine that an operation cannot be performed. For this reason, the process of pressing the login icon can be executed, but the process of pressing a different icon other than the login icon cannot be executed.

A command according to which processing can always be executed regardless of the state of the control unit 120 may skip step S304. Generally, whether processing can be executed is defined with respect to each API.

In step S305, the control unit 120 executes processing according to the particular processing request. In the execution of the processing, the control unit 120 performs control to simulate a situation where the operator operates the screen. For example, as illustrated in FIGS. 3A and 3B, in the case of a command to allow the operator to perform the process of inputting a user name and a password and pressing the login icon, the control unit 120 performs the process of inputting information of which the control unit 120 is notified as a command to the text box for the user name, and also performs the process of inputting information of which the control unit 120 is notified as a command to the text box for the password. Finally, the control unit 120 executes the process of clicking the login icon. Further, in another method, the processing execution unit 121 has a processing logic that operates when the login icon is clicked after the user name and the password are input. This processing logic may be directly called.

In step S306, the control unit 120 notifies the second terminal apparatus 203 of the processing result of the control unit 120. If the processing is successful, the control unit 120 notifies the second terminal apparatus 203 of the success. If the processing has failed, the control unit 120 notifies the second terminal apparatus 203 of the failure. Although there are various reasons as the reason for the failure of the processing, the control unit 120 may notify the second terminal apparatus 203 of the failure to the extent that the control unit 120 can notify the second terminal apparatus 203. At this time, if the control unit 120 is controlled according to the processing request output from the second terminal apparatus 203, the right to control the control unit 120 owned by the second terminal apparatus 203 is transferred to the first terminal apparatus 201.

As described above, if a processing request is output from the second terminal apparatus 203, the right to control the control unit 120 owned by the first terminal apparatus 201 is transferred to the second terminal apparatus 203. If the control unit 120 is controlled based on the processing request, the right to control the control unit 120 owned by the second terminal apparatus 203 is transferred to the first terminal apparatus 201. That is, the first terminal apparatus 201 always owns the right to control the control unit 120. If a processing request is output from the second terminal apparatus 203, the second terminal apparatus 203 transfers the right to control the control unit 120 from the first terminal apparatus 201. Then, if the control unit 120 is controlled according to the processing request output from the second terminal apparatus 203, the second terminal apparatus 203 transfers the right to control the control unit 120 to the first terminal apparatus 201.

As the control of the radiographic imaging apparatuses 102 and 103, login control is described. When imaging is performed using the radiographic imaging apparatuses 102 and 103, and if an examination input screen is displayed on the display unit 202, an examination selection process and an examination start process can be executed, but another process (e.g., a login process) cannot be executed. Further, if an imaging screen for performing imaging using the radiographic imaging apparatuses 102 and 103 is displayed, image processing and an examination end process can be executed, but another process (e.g., a login process, an examination selection process, or an examination start process) cannot be executed.

Further, if a plurality of processing requests is output from the second terminal apparatus 203, the second terminal apparatus 203 transfers the right to control the control unit 120 from the first terminal apparatus 201 with respect to each processing request. Then, if a single processing request is processed, the second terminal apparatus 203 transfers the right to control the control unit 120 to the first terminal apparatus 201. For example, if the plurality of processing requests is two processing requests, the control right is transferred twice. If the plurality of processing requests is three processing requests, the control right is transferred three times.

In a case where a plurality of processing requests output from the second terminal apparatus 203 is relevant to each other, e.g., in a case where all the plurality of processing requests is related to login control, the second terminal apparatus 203 may transfer the right to control the control unit 120 to the first terminal apparatus 201 after a series of operations of control is executed on the control unit 120 according to the plurality of processing requests output from the second terminal apparatus 203. That a plurality of processing requests is relevant to each other means that, for example, even if the plurality of processing requests is executed, the screen does not transition.

As described above, to perform processing through the second terminal apparatus 203, the second terminal apparatus 203 acquires the right to control the control unit 120 from the first terminal apparatus 201, and the control unit 120 controls the radiographic imaging apparatuses 102 and 103 based on a processing request from the second terminal apparatus 203. In this way, even if operations based on a plurality of terminal apparatuses occur, it is possible to avoid the collision of the operations.

Figure 5:
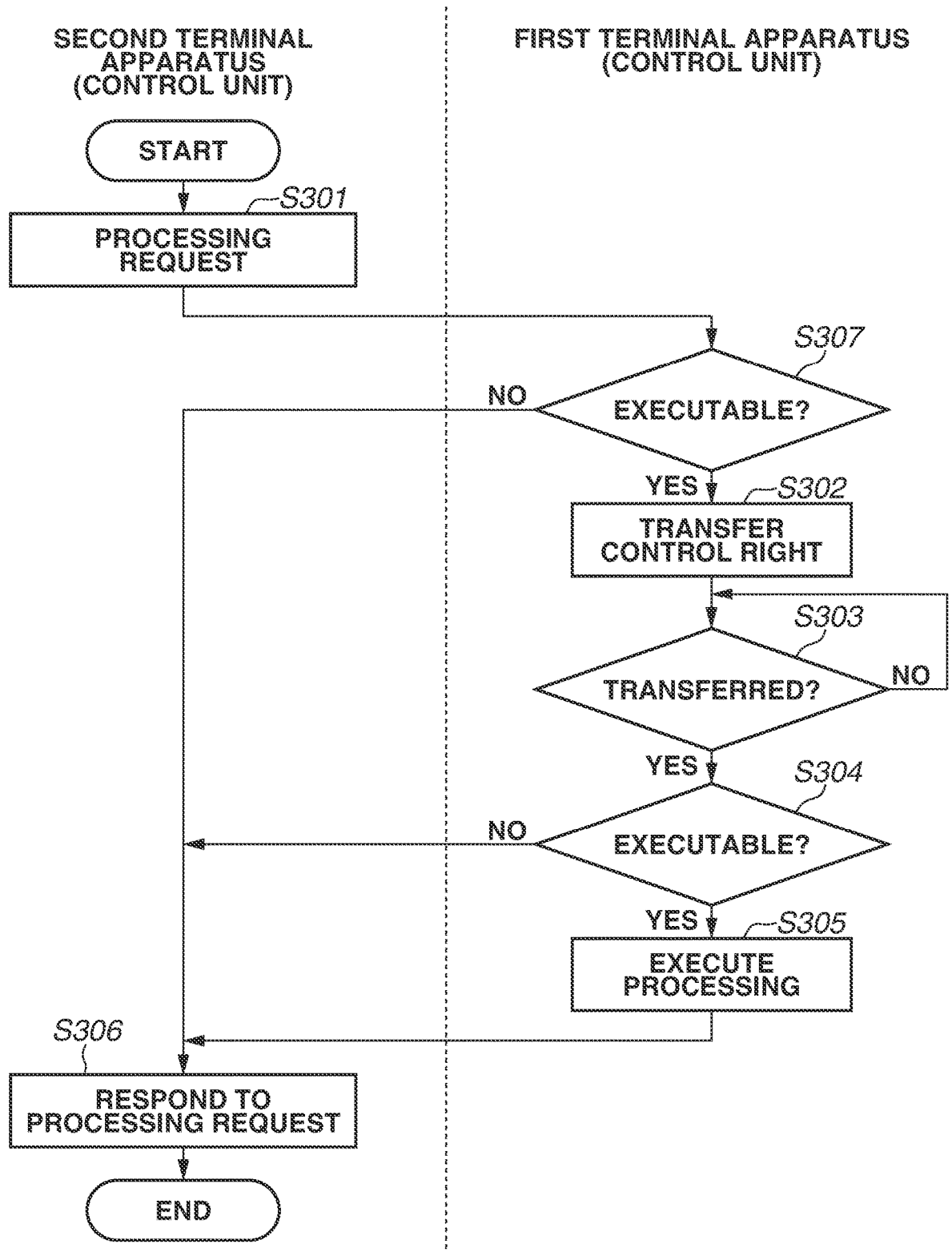
FIG. 5 is a flowchart illustrating an operation form of the radiographic imaging system according to the first exemplary embodiment.

Next, with reference to a flowchart in FIG. 5, an operation form of the radiographic imaging system is described. FIG. 5 is different from FIG. 4 in that before the control right is transferred, it is determined whether a command can be executed. Steps S301 to S306 are similar to those in FIG. 4.

In step S307, before the control right is transferred in step S302, the determination unit 136 determines whether a command can be executed. The content of the determination is similar to that in step S304. If the transfer of the control right has failed in step S303, the second terminal apparatus 203 may wait for the control right. There is no problem as long as the waiting is processing that does not affect the responsiveness of an application. However, in a case where the second terminal apparatus 203 waits for the control right for a slow process, a problem may arise in the responsiveness of the second terminal apparatus 203. In response, in a case where it is known in advance before the control right is transferred that processing cannot be performed, it should be determined in advance whether the processing can be executed, and then, the result of the determination should be returned.

In this way, before the control right is transferred, the determination unit 136 determines whether a command can be executed, whereby it is possible to reduce waiting.

Figure 6A:
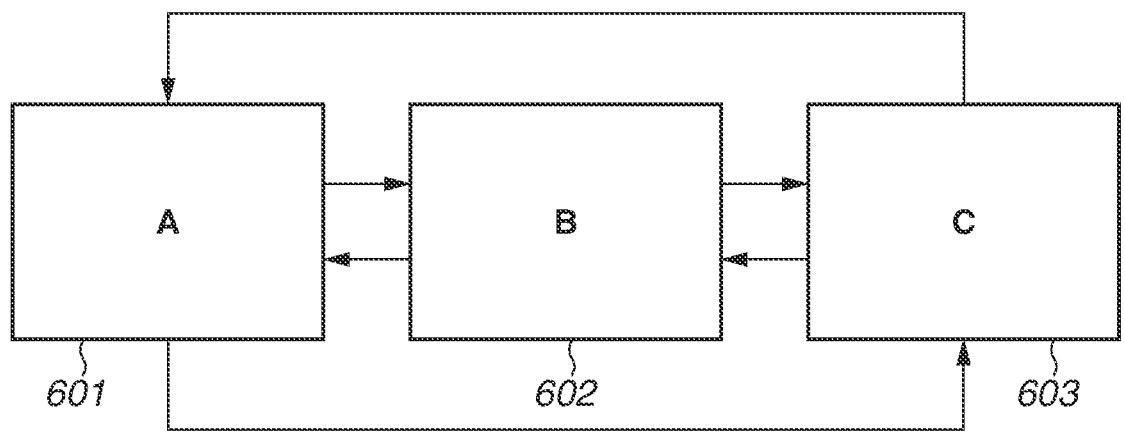
FIGS. 6A and 6B are diagrams illustrating an operation form of a radiographic imaging system according to a second exemplary embodiment.
Figure 6B:
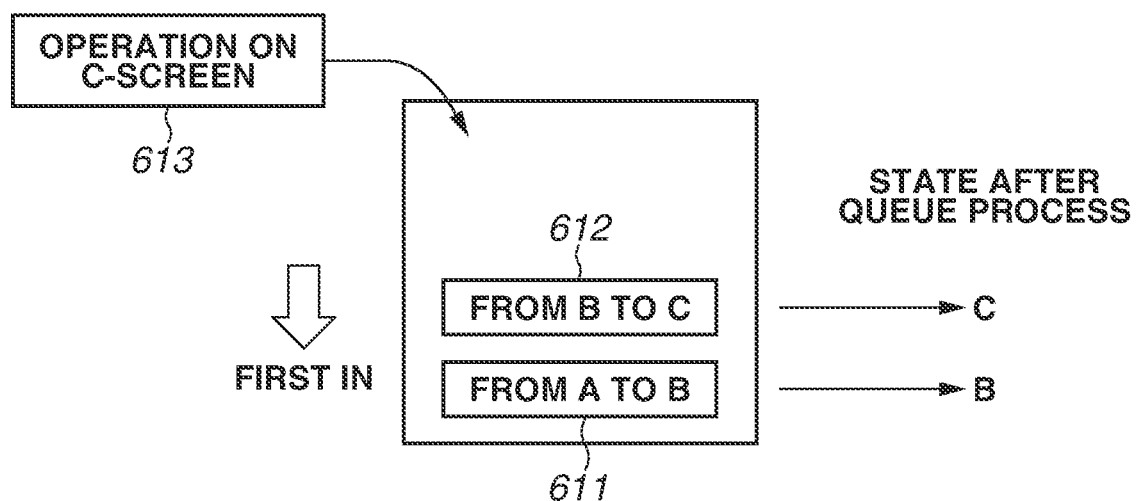

Next, with reference to FIGS. 6A and 6B, a second exemplary embodiment is described. The second exemplary embodiment is different from the first exemplary embodiment in that the control unit 120 includes the determination unit 136 that, based on the state of the control unit 120, determines whether a processing request output from the second terminal apparatus 203 can be executed. If a plurality of processing requests is output from the second terminal apparatus 203, then based on the state of the control unit 120 when the control unit 120 is controlled according to each processing request, the determination unit 136 determines whether the processing request can be executed.

The second state management unit 137 is a management unit that manages which state the control unit 120 will be in after a processing request accumulated in a queue is executed, as compared with the state of the control unit 120 held in the first state management unit 135 at the current time.

With reference to FIGS. 6A and 6B, a description is given. Suppose that the control unit 120 has the function of causing the state of the screen to transition as illustrated in FIG. 6.4. An A-screen 601 can transition to a B-screen 602 and a C-screen 603. The B-screen 602 can transition to the A-screen 601 and the C-screen 603. The C-screen 603 can transition to the A-screen 601 and the B-screen 602. If the current state is the A-screen 601, and a processing request 611 is a processing request to cause the A-screen 601 to transition to the B-screen 602 from the current state, the state of the screen after the processing request 611 is processed is the B-screen 602. If a processing request 612 following the processing request 611 is a processing request to cause the B-screen 602 to transition to the C-screen 603, the state of the screen after the processing request 612 is processed is the C-screen 603. Next, if a processing request 613 is an operation on the C-screen 603, the state of the screen when processing on all the queued processing requests in a queue is completed is the C-screen 603. Thus, an operation on the C-screen 603 can be performed. If the processing request 613 can be processed, the processing request 613 is queued. If the processing request 613 is, for example, a processing request regarding the A-screen 601, the processing request 613 cannot be processed, and therefore is not allowed to be queued.

In other words, based on the state where the screen is changed according to the previous processing request, the determination unit 136 determines whether a processing request can be executed. For example, if the state of the screen after the previous processing request is processed is the C-screen 603, the determination unit 136 determines that a processing request regarding the C-screen 603 can be executed. Further, if the state of the screen after the previous processing request is processed is the C-screen 603, the determination unit 136 determines that a processing request regarding the A-screen 601 or the B-screen 602 cannot be executed.

Figure 7:
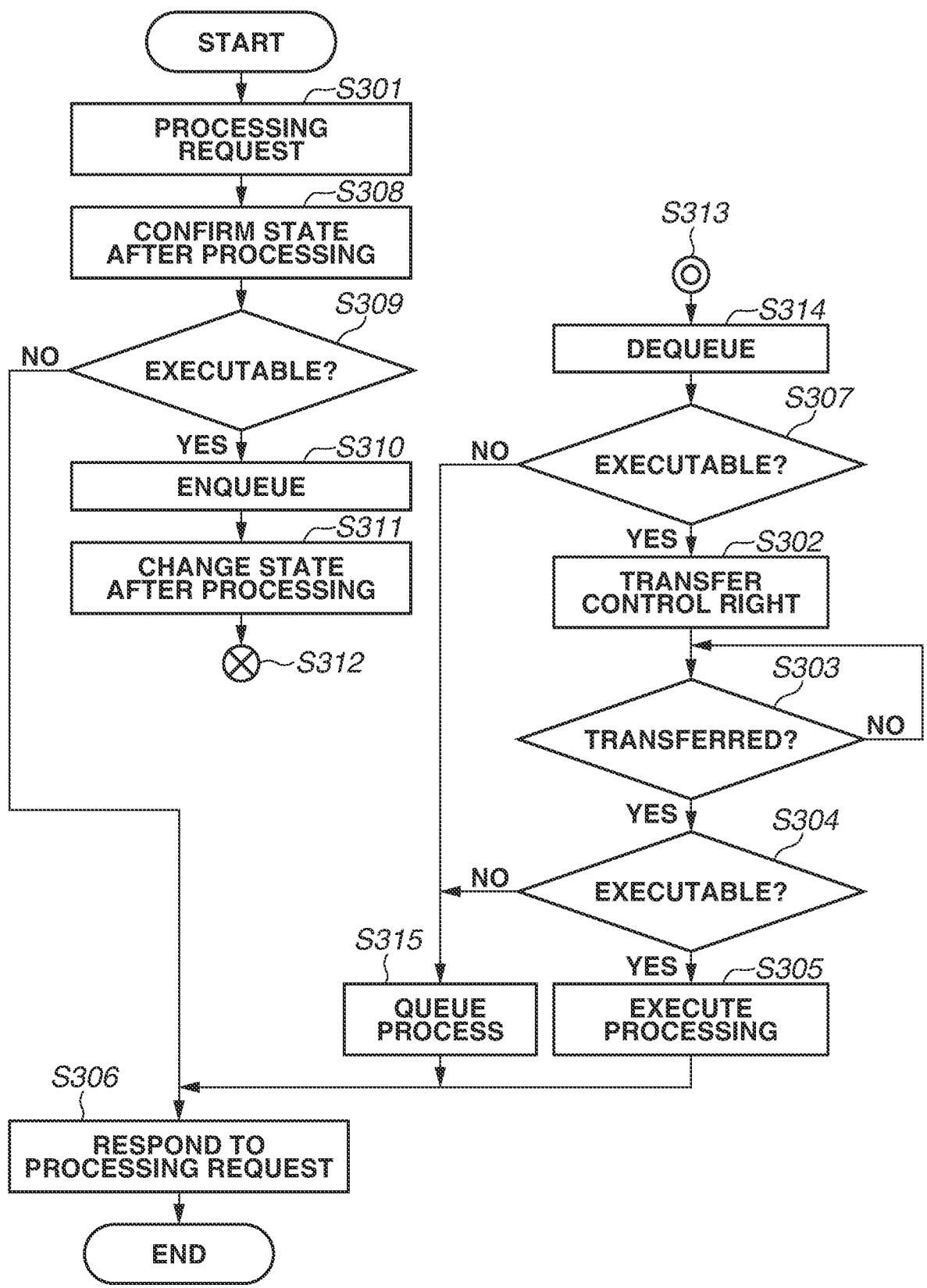
FIG. 7 is a flowchart illustrating an operation form of the radiographic imaging system according to the second exemplary embodiment.

FIG. 7 is a flowchart illustrating an operation form of a radiographic imaging system according to the second exemplary embodiment. Portions described with reference to FIGS. 4 and 5 are not described here.

In step S308, the determination unit 136 determines whether processing can be executed in the state after the processing request in step S301 is processed. If processing can be executed, then in step S309, it is determined that processing can be executed (Yes in step S309). Then, in step S310, the processing request is enqueued. If it is determined in step S309 that processing cannot be executed (No in step S309), the processing request cannot be processed. Thus, in step S306, the control unit 120 responds to the processing request to the effect that processing cannot be executed.

Next, if the processing request management unit 131 enqueues the processing request in step S310, the state after a queue process may be changed due to the enqueued processing. In response, the processing request management unit 131 reflects the change in the state due to the enqueued processing on the state after a queue process. If the processing request management unit 131 enqueues the processing request, the flow of queueing ends in step S312. The order of steps S310 and S311 is a design matter, and therefore, either of steps S310 and S311 can be performed first as long as the order is designed to avoid inconsistency.

In step S314, if a next processing request in the queue becomes able to be processed, the processing request management unit 131 dequeues the queued processing request in the queue in an FIFO manner. In step S307, the determination unit 136 determines whether the processing request can be executed. Normally, the processing request should be able to be processed because the processing request is queued after the state after a queue process is confirmed. In this system, however, the first terminal apparatus 201 and the second terminal apparatus 203 operate cooperatively with each other, and therefore may not be able to operate.

For example, suppose that as illustrated in FIG. 6B, the B-screen 602 is displayed by processing the processing request 611. Next, for example, if the state of the B-screen 602 transitions to the A-screen 601 by an operation on the first terminal apparatus 201 before the processing request 612 is processed, the processing request 612 cannot be executed. For this reason, in step S307, the determination unit 136 determines whether the processing request can be executed. If it is determined in step S307 that the processing request cannot be executed (No in step S307), the state where a next processing request is dequeued is inconsistent. Thus, in step S315, the processing request management unit 131 performs a queue process. The queue process in step S315 is, for example, the process in which the processing request management unit 131 processes all the queued processing requests in the queue as not being able to be processed, or the process in which the control unit 120 adds processing for causing the screen to transition to be consistent with the current state, or the process in which the processing request management unit 131 skips some queue processes, thereby controlling the state of the queue process to be consistent.

Figure 8:
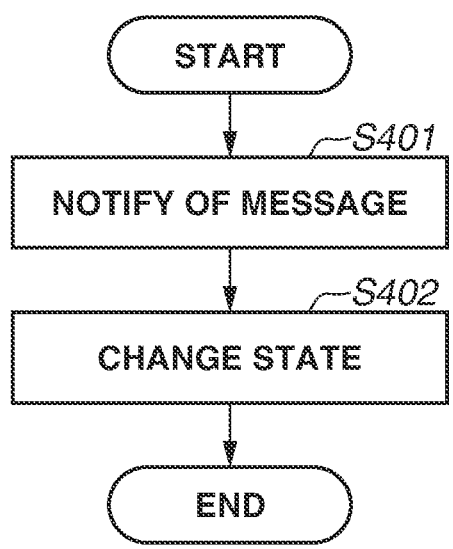
FIG. 8 is a flowchart illustrating an operation form of the radiographic imaging system to manage a message.

FIG. 8 is a flowchart illustrating an operation form regarding the management of a message. A description is given of the first state management unit 135 that is notified of a message that the state of the control unit 120 changes, and manages the state of the control unit 120 based on the notified message.

In step S401, the control unit 120 notifies the message acquisition unit 134 that the state of the control unit 120 changes. The message acquisition unit 134 notifies the first state management unit 135 of the notified information. In step S402, the first state management unit 135 changes the state of the control unit 120 managed by the first state management unit 135. In the examples of FIGS. 6A and 6B, if the processing request 611 is processed, the state of the A-screen 601 transitions to the B-screen 602. At this time, the control unit 120 gives a notification, as a message, that the state of the screen transitions to the B-screen 602. The first state management unit 135 manages the state where the A-screen 601 is changed to the B-screen 602. Then, the control unit 120 changes the state of the displayed screen.

Next, with reference to FIGS. 9A to 11, a third exemplary embodiment described. The third exemplary embodiment is different from the first and second exemplary embodiments in that the state of the radiographic imaging apparatus 102 is changed using the first terminal apparatus 201 or the second terminal apparatus 203, and the control unit 120 notifies the first terminal apparatus 201 and the second terminal apparatus 203 of the changed state of the radiographic imaging apparatus 102. A description is given here on the assumption that the radiographic imaging apparatus 102 is a control target. Alternatively, the radiographic imaging apparatus 103 may be the control target.

In this case, to change the state of the radiographic imaging apparatus 102 through the second terminal apparatus 203, the second terminal apparatus 203 transfers the right to control the control unit 120 from the first terminal apparatus 201. Then, if the state of the radiographic imaging apparatus 102 is changed through the second terminal apparatus 203, the second terminal apparatus 203 transfers the right to control the control unit 120 to the first terminal apparatus 201.

Figure 9B:
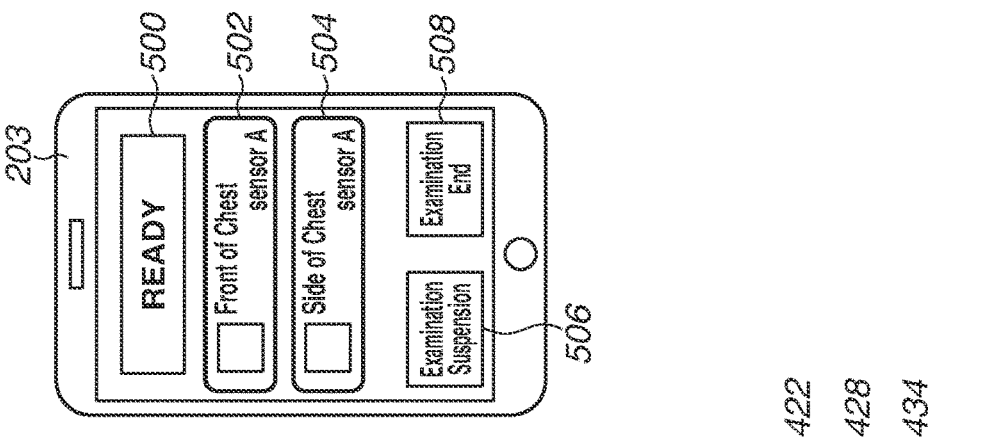
FIGS. 9A and 9B are diagrams illustrating screens of a radiographic imaging system according to a third exemplary embodiment.
Figure 9A:
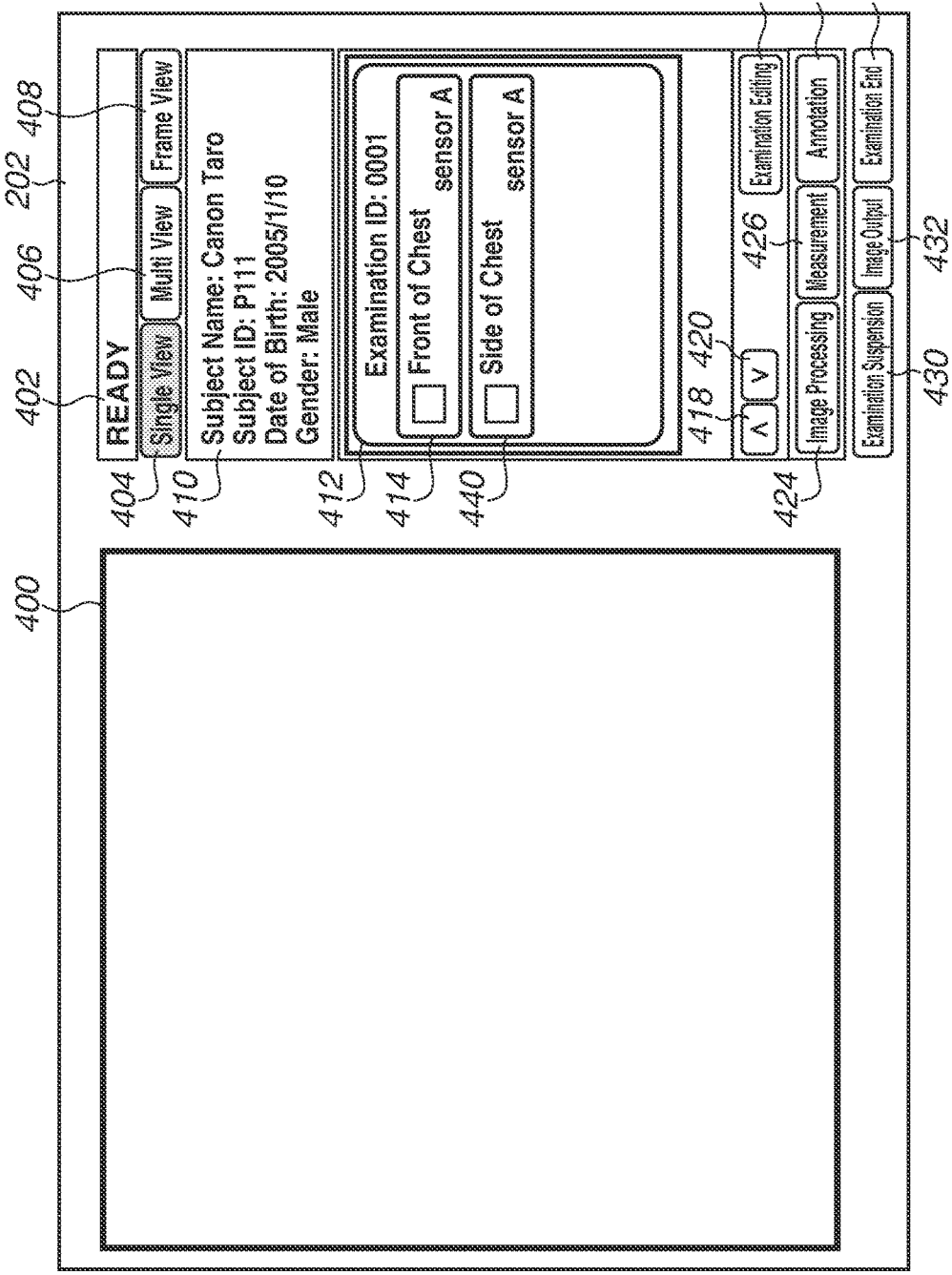

FIGS. 9A and 9B illustrate the screens of the display unit 202 of the first terminal apparatus 201 and the second terminal apparatus 203. FIG. 9A illustrates the screen of the display unit 202 of the first terminal apparatus 201. FIG. 9A illustrates the screen of the display unit 202 before imaging is performed. The control unit 120 can control the screen of the display unit 202 via the first terminal apparatus 201. The screen of the display unit 202 includes an image display area 400 for displaying a radiographic image, The screen of the display unit 202 includes a status display area 402 for displaying the status of the radiographic imaging apparatus 102, a single view icon 404, a multi view icon 406, and a frame view icon 408.

The screen of the display unit 202 includes a subject display area 410 for displaying subject information, and an examination information display area 412 for displaying examination information. The examination information display area 412 includes imaging procedure icons 414 and 440 for displaying and executing imaging procedures. The imaging procedure icons 414 and 440 can also be said to be imaging protocols.

Further, the screen of the display unit 202 includes a moving-up-in-order icon 418, a moving-down-in-order icon 420, an examination editing icon 422, an image processing icon 424, a measurement icon 426, an annotation editing icon 428, an examination suspension icon 430, an image output icon 432, and an examination end icon 434.

In the image display area 400, a captured radiographic image is displayed. In a case where the display target is replaced after imaging is performed, a selected radiographic image is displayed. In the image display area 400, subject information, examination information, or an imaging condition may be displayed as necessary.

The status display area 402 is an area where the status of the radiographic imaging apparatus 102 is displayed by differentiating colors or characters to make it easy for the operator to distinguish the status of the radiographic imaging apparatus 102.

Upon receiving the status from the radiographic imaging apparatus 102, the control unit 120 notifies the display unit 202 of the status. For example, if the radiographic imaging apparatus 102 cannot perform imaging, "not ready" is displayed in the status display area 402. Further, if the radiographic imaging apparatus 102 can perform imaging, "ready" is displayed in the status display area 402. The background color of "ready" is changed to a color distinguishable from the background color of "not ready". In the status display area 402, the state of the radiographic imaging apparatus 102 is displayed.

The single view icon 404 is an icon for changing to a single view for displaying a single frame of a selected radiographic image in the image display area 400. In a case where an image has a plurality of frames, then by performing an operation on the first terminal apparatus 201 while a preview is displayed, it is also possible to display another frame or reproduce a moving image. The multi view icon 406 is an icon for changing to a multi-view which is obtained by dividing the image display area 400 into a plurality of display areas in a grid and in which a group of images captured in an examination that is being executed is displayed in parallel. The frame view icon 408 is an icon for changing to a frame view which is obtained by dividing the image display area 400 into a plurality of display areas in a grid and in which a group of frame images of a moving image is displayed in parallel.

The subject display area 410 is an area where subject information such as a subject name, a subject identification (ID), a date of birth, and gender is displayed. Further, in the examination information display area 412, an examination ID regarding imaging and the imaging procedure icons 414 and 440 including imaging procedures are displayed. In each of the imaging procedure icons 414 and 440, an imaging procedure including the name of the imaging procedure and the name of a radiographic imaging apparatus, and if imaging is executed, a thumbnail for a radiographic image are displayed. Further, before imaging is executed, a thumbnail representing the imaging orientation is displayed. The thumbnail representing the imaging orientation includes information regarding the stand 301, which supports the radiographic imaging apparatus 102. Accordingly, the operator confirms the display content of the thumbnail and thereby can understand whether imaging based on this imaging procedure is executed.

In this case, in the imaging procedure regarding the imaging procedure icon 414 (the front of the chest), image processing will be executed on a radiographic image captured by the imaging procedure regarding the imaging procedure icon 414 (the front of the chest). In the imaging procedure regarding the imaging procedure icon 440 (the side of the chest), image processing will be executed on a radiographic image captured by the imaging procedure regarding the imaging procedure icon 440 (the side of the chest).

The moving-up-in-order icon 418 is an icon for giving an instruction to move up in the order of the planned execution of the imaging procedures. The moving-down-in-order icon 420 is an icon for giving an instruction to move down in the order of the planned execution of the imaging procedures. The examination editing icon 422 is an icon for giving an instruction to transition to a "various settings" screen. The image processing icon 424 is an icon for giving an instruction to change the displaying and hiding of image processing. The measurement icon 426 is an icon for giving an instruction to change the displaying and hiding of a measurement operation function. The annotation editing icon 428 is an icon for giving an instruction to change the displaying and hiding of an annotation. The examination suspension icon 430 is an icon for giving an instruction to suspend an examination that is being executed. The image output icon 432 is an icon for giving an instruction to output a radiographic image included in an examination that is being executed. The examination end icon 434 is an icon for receiving an operation input for ending an examination including at least one imaging operation, FIG. 9B illustrates the screen of the second terminal apparatus 203. The second terminal apparatus 203 can display a part of the screen displayed on the display unit 202 of the first terminal apparatus 201.

The second terminal apparatus 203 displays a status display area 500 for indicating the state of the radiographic imaging apparatus 102, imaging procedure icons 502 and 501 including imaging procedures, an examination suspension icon 506 for giving an instruction to suspend an examination that is being executed, and an examination end icon 508 for receiving an operation input for ending an examination. The states of the status display area 500 and the imaging procedure icons 502 and 504 displayed on the second terminal apparatus 203 are similar to those of the status display area 402 and the imaging procedure icons 414 and 440, respectively, displayed on the display unit 202 of the first terminal apparatus 201.

If the radiographic imaging apparatus 102 can perform imaging, the control unit 120 notifies the first terminal apparatus 201 and the second terminal apparatus 203 that the radiographic imaging apparatus 102 can perform imaging. At this time, the control unit 120 also notifies the message acquisition unit 134 that the radiographic imaging apparatus 102 can perform imaging. The first state management unit 135 manages the state where the radiographic imaging apparatus 102 can perform imaging. At this time, a processing request regarding imaging in the processing request management unit 131 can be executed. Then, "ready" is displayed in each of the status display area 402 of the display unit 202 of the first terminal apparatus 201 and the status display area 500 of the second terminal apparatus 203.

At this time, if the radiographic imaging apparatus 102 enters the state where the radiographic imaging apparatus 102 cannot perform imaging, the control unit 120 notifies the first terminal apparatus 201 and the second terminal apparatus 203 that the radiographic imaging apparatus 102 cannot perform imaging. At this time, the control unit 120 also notifies the message acquisition unit 134 that the radiographic imaging apparatus 102 cannot perform imaging. The first state management unit 135 manages the state where the radiographic imaging apparatus 102 cannot perform imaging. At this time, a processing request regarding imaging in the processing request management unit 131 cannot be executed. Then, as illustrated in FIGS. 10A and 10B, "not ready" is displayed in each of the status display area 402 of the display unit 202 of the first terminal apparatus 201 and the status display area 500 of the second terminal apparatus 203. The background color of "ready" and the background color of "not ready" may be changed to colors distinguishable from each other.

Figure 11:
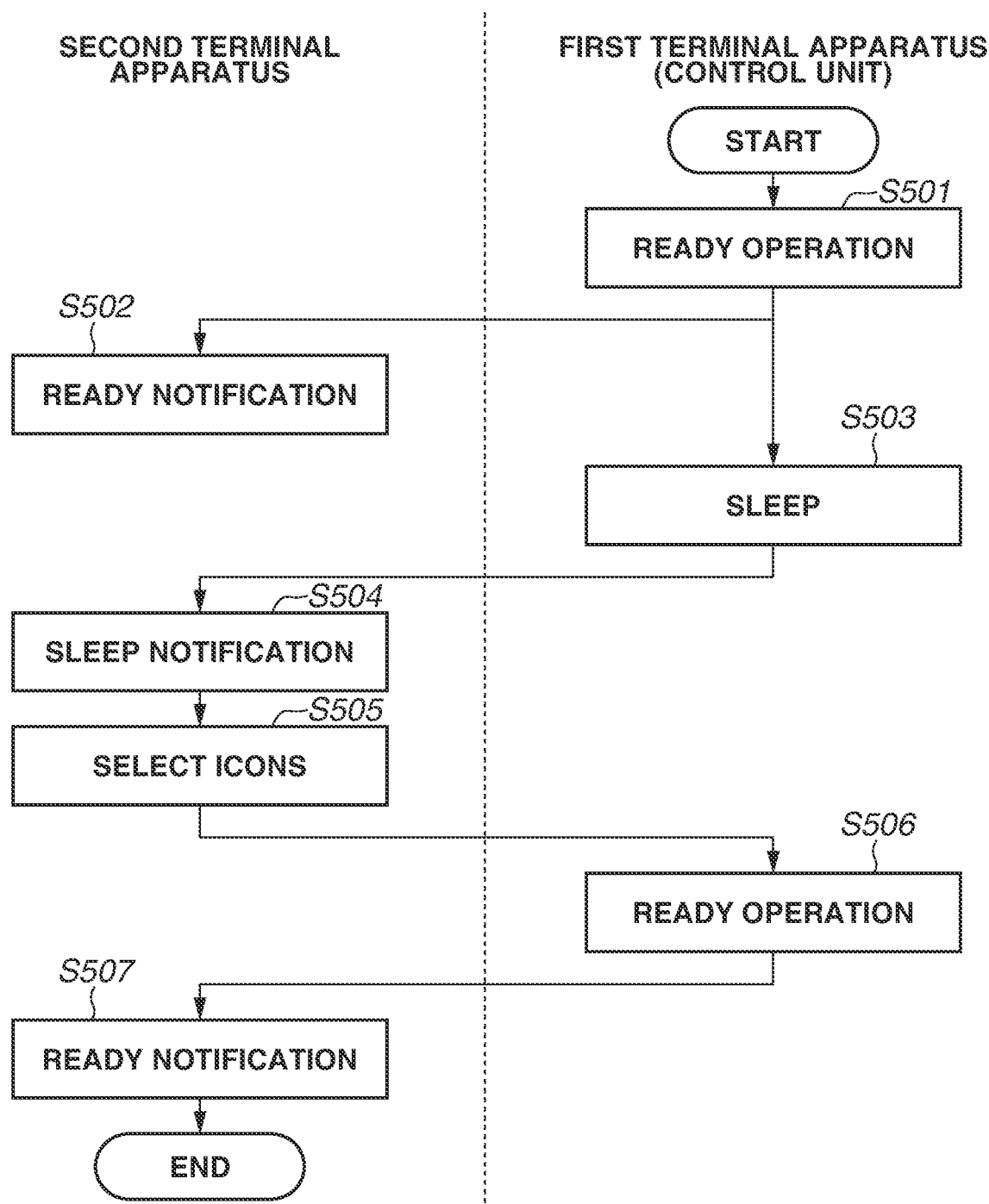
FIG. 11 is a flowchart illustrating an operation form of the radiographic imaging system according to the third exemplary embodiment.

FIG. 11 is a flowchart illustrating an operation form of a radiographic imaging system according to the third exemplary embodiment.

In step S501, using the first terminal apparatus 201, the operator enables the radiographic imaging apparatus 102 to perform imaging. That is, the operator performs a ready operation on the radiographic imaging apparatus 102.

In step S502, if the radiographic imaging apparatus 102 is enabled to perform imaging, the control unit 120 notifies the second terminal apparatus 203 that the radiographic imaging apparatus 102 can perform imaging. That is, the control unit 120 gives a ready notification to the second terminal apparatus 203 and also gives a ready notification to the first terminal apparatus 201, "Ready" is displayed in each of the status display area 402 of the display unlit 202 of the first terminal apparatus 201 and the status display area 500 of the second terminal apparatus 203. At this time, imaging may be performed using the radiographic imaging apparatus 102, and the operation may end.

In step S503, after the ready operation is performed on the radiographic imaging apparatus 102, and if a predetermined time (e.g., 10 minutes) elapses from the ready operation, the radiographic imaging apparatus 102 enters a sleep state where the radiographic imaging apparatus 102 cannot perform imaging. The control unit 120 brings the radiographic imaging apparatus 102 into the sleep state where the radiographic imaging apparatus 102 cannot perform imaging.

In step S504, if the radiographic imaging apparatus 102 enters the state where the radiographic imaging apparatus 102 cannot perform imaging, the control unit 120 notifies the second terminal apparatus 203 that the radiographic imaging apparatus 102 cannot perform imaging. The control unit 120 may notify the first terminal apparatus 201 that the radiographic imaging apparatus 102 cannot perform imaging. That is, the control unit 120 gives a sleep notification to the second terminal apparatus 203. "Not ready" is displayed in the status display area 500 of the second terminal apparatus 203.

In step S505, the operator selects the icons 502 and 504 regarding imaging procedures using the second terminal apparatus 203. At this time, the right to control the control unit 120 is transferred from the first terminal apparatus 201 to the second terminal apparatus 203. The second terminal apparatus 203 notifies the control unit 120 that the icons 502 and 504 regarding imaging procedures are selected in the second terminal apparatus 203.

In step S506, the control unit 120 enables the radiographic imaging apparatus 102 to perform imaging. As described above, the operator can perform a ready operation on the radiographic imaging apparatus 102 via the second terminal apparatus 203.

In step S507, if the radiographic imaging apparatus 102 is enabled to perform imaging, the control unit 120 notifies the second terminal apparatus 203 that the radiographic imaging apparatus 102 changes from the state where the radiographic imaging apparatus 102 cannot perform imaging to the state where the radiographic imaging apparatus 102 can perform imaging. The control unit 120 may notify the first terminal apparatus 201 that the radiographic imaging apparatus 102 perform imaging. That is, the control unit 120 gives a ready notification to the second terminal apparatus 203 and also gives a ready notification to the first terminal apparatus 201, "Ready" is displayed in each of the status display area 402 of the display unit 202 of the first terminal apparatus 201 and the status display area 500 of the second terminal apparatus 203. At this time, imaging is performed using the radiographic imaging apparatus 102, and the operation ends.

As described above, the control unit 120 notifies the second terminal apparatus 203 of the changed state of the radiographic imaging apparatus 102. Thus, the operator carrying the second terminal apparatus 203 can understand the state of the radiographic imaging apparatus 102.

Next, with reference to FIGS. 12A, 12B, and 13, a fourth exemplary embodiment is described. The fourth exemplary embodiment is different from the first to third exemplary embodiments in that a rejection reason for rejecting a radiographic image captured by the radiographic imaging apparatus 102 is set using the second terminal apparatus 203, and the rejection reason is shared with the first terminal apparatus 201.

In this case, to set a rejection reason for rejecting a radiographic image through the second terminal apparatus 203, the second terminal apparatus 203 transfers the right to control the control unit 120 from the first terminal apparatus 201. Then, if the rejection reason for rejecting the radiographic image is set through the second terminal apparatus 203, the second terminal apparatus 203 transfers the right to control the control unit 120 to the first terminal apparatus 201.

FIG. 12A illustrates the screen of the display unit 202 of the first terminal apparatus 201. FIG. 12B illustrates the screen of the second terminal apparatus 203. Since these screens are described in the third exemplary embodiment, the differences from the third exemplary embodiment are mainly described.

In FIG. 12A, a radiographic image is displayed in the image display area 400 of the display unit 202 of the first terminal apparatus 201. If the operator determines that there is a rejection reason, such as body movement, low dose (insufficient dose), or high dose (excessive dose), for rejecting the radiographic image, the operator presses a rejection icon 450. At this time, a rejection reason selection screen 460 for selecting a rejection reason is displayed.

On the rejection reason selection screen 460, a plurality of types of rejection reason candidates is displayed. The operator selects any rejection reason candidate from these rejection reason candidates and thereby can input a rejection reason for the radiographic image. On the rejection reason selection screen 460, rejection reason candidates such as body movement 452, low dose (insufficient dose) 454, and high dose (excessive dose) 456 are displayed.

As illustrated in the upper part of FIG. 12B, a radiographic image is displayed in an image display area 552 of the second terminal apparatus 203. If the operator determines that there is a rejection reason, such as body movement, low dose (insufficient dose), or high dose (excessive dose), for rejecting the radiographic image, the operator presses a rejection icon 550. At this time, as illustrated in the lower part of FIG. 12B, the second terminal apparatus 203 transitions to a rejection reason selection screen for selecting a rejection reason.

On the second terminal apparatus 203, a plurality of types of rejection reason candidates is displayed. The operator selects any rejection reason candidate from these rejection reason candidates and presses a setting icon 554 and thereby can input a rejection reason for the radiographic image. At this time, rejection reason candidates such as body movement 556, low dose (insufficient dose) 558, and high dose (excessive dose) 560 are displayed.

FIG. 13 is a flowchart illustrating an operation form of a radiographic imaging system according to the fourth exemplary embodiment.

In step S601, the operator performs radiographic imaging using the first terminal apparatus 201 and the radiographic imaging apparatus 102. The image acquisition unit 122 of the control unit 120 acquires a radiographic image (image data) output from the radiographic imaging apparatus 102. The control unit 120 outputs the radiographic image to the first terminal apparatus 201 and the second terminal apparatus 203.

In step S602, the second terminal apparatus 203 displays the radiographic image captured by the radiographic imaging apparatus 102. The display unit 202 of the first terminal apparatus 201 may also display the radiographic image captured by the radiographic imaging apparatus 102.

In step S603, if the operator determines that there is a rejection reason, such as body movement, low dose (insufficient dose), or high dose (excessive dose), for rejecting the radiographic image displayed in the image display area 552 of the second terminal apparatus 203, the operator presses the rejection icon 550. At this time, the right to control the control unit 120 is transferred from the first terminal apparatus 201 to the second terminal apparatus 203.

In step S604, a plurality of types of rejection reason candidates is displayed on the second terminal apparatus 203. The operator selects any rejection reason candidate from these rejection reason candidates and presses the setting icon 554, thereby selecting a rejection reason for the radiographic image. The second terminal apparatus 203 notifies the control unit 120 of the selected rejection reason.

In step S605, the control unit 120 performs a rejection process on the radiographic image. The control unit 120 stores the rejection reason and the radiographic image in association with each other in the memory of the control unit 120. The control unit 120 can also notify the first terminal apparatus 201 of the rejection reason associated with the radiographic image. The display unit 202 of the first terminal apparatus 201 can also display the rejection reason set using the second terminal apparatus 203.

Figure 14B:
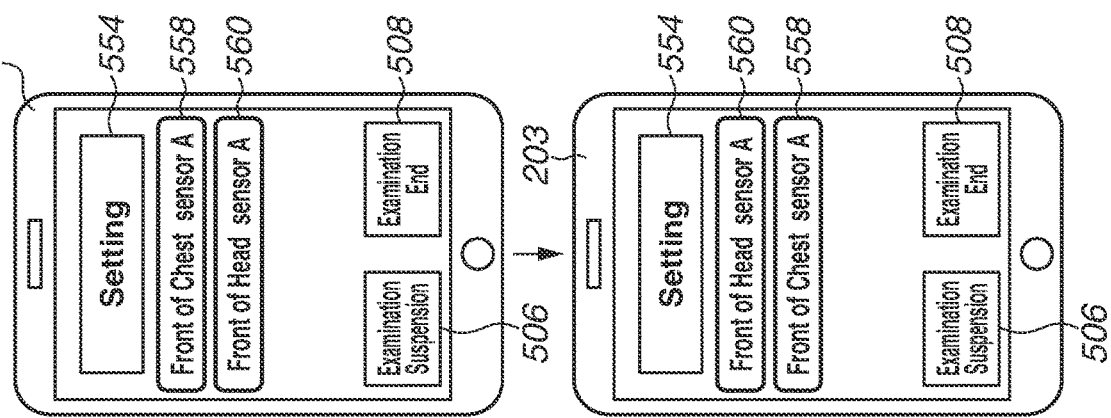
FIGS. 14A and 14B are diagrams illustrating screens of a radiographic imaging system according to a fifth exemplary embodiment.
Figure 14A:
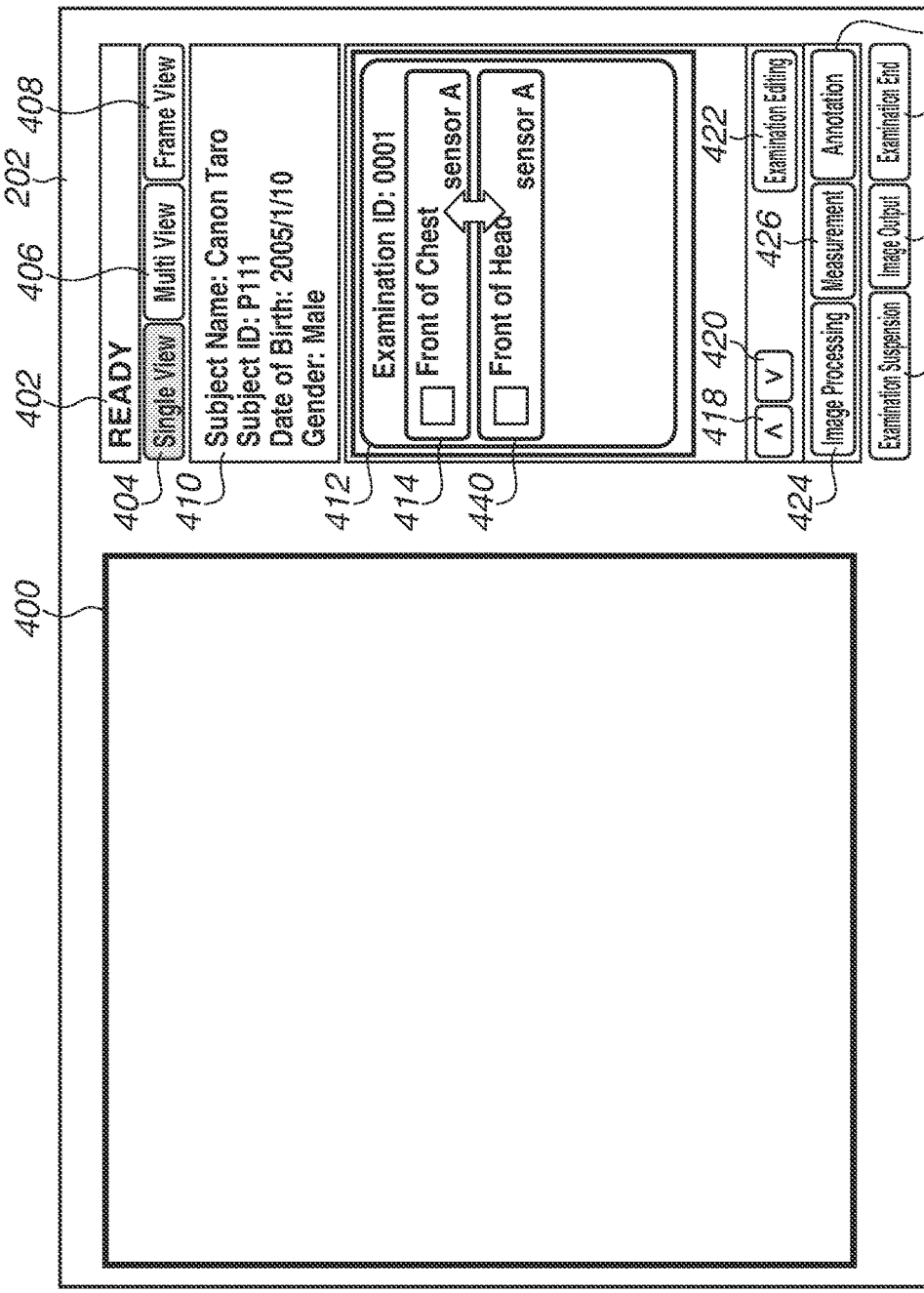

Next, with reference to FIGS. 14A, 14B, and 15, a fifth exemplary embodiment is described. The fifth exemplary embodiment is different from the first to fourth exemplary embodiments in that the order of imaging procedures is changed using the second terminal apparatus 203, and the changed order of imaging procedures is shared with the first terminal apparatus 201.

In this case, to change the order of imaging procedures through the second terminal apparatus 203, the second terminal apparatus 203 transfers the right to control the control unit 120 from the first terminal apparatus 201. Then, if the order of imaging procedures is changed through the second terminal apparatus 203, the second terminal apparatus 203 transfers the right to control the control unit 120 to the first terminal apparatus 201.

FIG. 14A illustrates the screen of the display unit 202 of the first terminal apparatus 201. FIG. 14B illustrates the screen of the second terminal apparatus 203. Since these screens are described in the third exemplary embodiment, the differences from the third exemplary embodiment are mainly described.

As illustrated in the upper part of FIG. 14B, the second terminal apparatus 203 displays imaging procedure icons 558 and 560 including imaging procedures, the examination suspension icon 506 for giving an instruction to suspend an examination that is being executed, and the examination end icon 508 for receiving an operation input for ending an examination. The imaging procedure icon 558 is an icon indicating an imaging procedure for the front of the chest. The imaging procedure icon 560 is an icon indicating an imaging procedure for the front of the head.

In this case, the operator replaces the imaging procedure icons 558 and 560 using the second terminal apparatus 203. After replacing the imaging procedure icons 558 and 560, the operator presses the setting icon 554, thereby the setting is to be executed. If the imaging procedure icons 558 and 560 are replaced, a setting is made so that, as illustrated in the lower part of FIG. 14B, the front of the head is to be captured first, and the front of the chest is to be captured next.

The second terminal apparatus 203 notifies the control unit 120 that the imaging procedure icons regarding imaging procedures are replaced. The control unit 120 notifies the first terminal apparatus 201 that the imaging procedure icons regarding imaging procedures are replaced. The display unit 202 of the first terminal apparatus 201 replaces the imaging procedure icon 414 indicating the imaging procedure for the front of the chest and the imaging procedure icon 440 indicating the imaging procedure for the front of the head.

The order of imaging procedures is changed using the second terminal apparatus 203, and the changed order of imaging procedures is shared with the first terminal apparatus 201, whereby it is possible to appropriately change the order of imaging procedures and perform imaging.

FIG. 15 is a flowchart illustrating an operation form of a radiographic imaging system according to the fifth exemplary embodiment.

In step S701, the operator replaces the imaging procedure icons 558 and 560 using the second terminal apparatus 203. At this time, the right to control the control unit 120 is transferred from the first terminal apparatus 201 to the second terminal apparatus 203.

In step S702, the determination unit 136 determines whether the replacement of the imaging procedure icons can be executed. For example, when imaging is performed using the radiographic imaging apparatus 102, and if the examination input screen is displayed on the display unit 202, the replacement of the imaging procedure icons can be executed. If the imaging screen for performing imaging using the radiographic imaging apparatus 102 or the login screen is displayed, the replacement of the imaging procedure icons cannot be executed. If the replacement of the imaging procedure icons can be executed (Yes in step S702), the processing proceeds to step S704. If the replacement of the imaging procedure icons cannot be executed (No in step S702), the processing proceeds to step S703. If the replacement of the imaging procedure icons cannot be executed, the control unit 120 notifies the second terminal apparatus 203 that the replacement of the imaging procedure icons has failed.

In step S704, the imaging procedure icons 558 and 560 are replaced using the control unit 120. If the replacement of the imaging procedure icons is completed, the control unit 120 notifies the second terminal apparatus 203 that the replacement of the imaging procedure icons is successful.

In step S703, the second terminal apparatus 203 indicates whether the replacement of the imaging procedure icons is successful or has failed. If the replacement of the imaging procedure icons has failed, the control unit 120 changes the screen displayed on the display unit 202 of the second terminal apparatus 203 or the first terminal apparatus 201 to the examination input screen and performs a series of operations again.

In the above description, the radiographic imaging system is described as a type of the medical image capturing system. Alternatively, the medical image capturing system may be achieved by a computed tomography (CT) apparatus, a magnetic resonance imaging (MRI) apparatus, or an ultrasonic diagnosis apparatus. The medical image capturing system includes a medical image capturing apparatus that generates a medical image, and a control unit that controls the medical image capturing apparatus based on processing requests from a first terminal apparatus 201 and a second terminal apparatus 203. The second terminal apparatus 203 acquires (transfers) a right to control the control unit from the first terminal apparatus 201, and the control unit controls the medical image capturing apparatus based on a processing request from the second terminal apparatus 203. In a case where the control unit controls the medical image capturing apparatus based on a processing request from the second terminal apparatus 203, the first terminal apparatus 201 acquires (transfers) the right to control the control unit from the second terminal apparatus 203.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-011775, filed Jan. 26, 2018, which is hereby incorporated by reference herein in its entirety.

What is claimed is:
1. A radiographic imaging system comprising:
a radiographic imaging apparatus configured to generate a radiographic image based on radiation emitted from a radiation generating apparatus;
a control unit configured to control the radiographic imaging apparatus based on processing requests from a first terminal apparatus and a second terminal apparatus, wherein the second terminal apparatus is configured to acquire a right to control the control unit from the first terminal apparatus; and
a processing request management unit configured to manage a plurality of processing requests output from the second terminal apparatus,
wherein the control unit controls the radiographic imaging apparatus based on a processing request output from the second terminal apparatus,
wherein, in a case where the control unit has controlled the radiographic imaging apparatus based on the processing request output from the second terminal apparatus, the first terminal apparatus acquires the right to control the control unit from the second terminal apparatus, and
wherein, in a case where the plurality of processing requests is output from the second terminal apparatus, the processing request management unit manages the plurality of processing requests using a first-in-first-out structure.
2. The radiographic imaging system according to claim 1, wherein in a case where processing request is output from the second terminal apparatus, the right to control the control unit is transferred from the first terminal apparatus to the second terminal apparatus.

3. The radiographic imaging system according to claim 1, wherein in the case where the plurality of processing requests is output from the second terminal apparatus, the right to control the control unit is transferred from the first terminal apparatus to the second terminal apparatus with respect to each processing request.

4. The radiographic imaging system according to claim 1, wherein the first terminal apparatus always owns the right to control the control unit and, unit and in a case where the processing request is output from the second terminal apparatus, the second terminal apparatus transfers the right to control the control unit from the first terminal apparatus.

5. The radiographic imaging system according to claim 1, wherein in a case where a transfer of the right to control the control unit from the first terminal apparatus to the second terminal apparatus fails, the second terminal apparatus waits until the right to control the control unit owned by the first terminal apparatus is released.

6. The radiographic imaging system according to claim 1, further comprising a notification unit configured to notify the second terminal apparatus that a state of the control unit is changed.

7. The radiographic imaging system according to claim 1, further comprising:
a state management unit configured to manage a state of the control unit; and
a determination unit configured to determine, based on the state of the control unit, whether a processing request output from the second terminal apparatus is executable.

8. The radiographic imaging system according to claim 7, wherein, in a case where the processing request output from the second terminal apparatus is not executable due to a transition of the state of the control unit caused by an operation in the first terminal apparatus, the processing request management unit does not enqueue the processing request output from the second terminal apparatus.

9. The radiographic imaging system according to claim 1, wherein in a case where a state of the radiographic imaging apparatus has been changed using the first or second terminal apparatus, the control unit notifies the first and second terminal apparatuses of the changed state of the radiographic imaging apparatus.

10. The radiographic imaging system according to claim 1, wherein, in a case where the plurality of processing requests output from the second terminal apparatus is relevant to each other, the second terminal apparatus transfers the right to control the control unit to the first terminal apparatus after a series of operations of control is executed on the control unit according to the plurality of processing requests.

11. The radiographic imaging system according to claim 1, wherein, in a case where there is a rejection reason for rejecting a radiographic image captured by the radiographic imaging apparatus, the rejection reason is set using the second terminal apparatus, and the set rejection reason is shared with the first terminal apparatus.

12. The radiographic imaging system according to claim 1, wherein, in a case where an order of imaging procedures has been changed using the second terminal apparatus, the changed order of imaging procedures is shared with the first terminal apparatus.

13. A medical image capturing system comprising:
a medical image capturing apparatus configured to generate a medical image;
a control unit configured to control the medical image capturing apparatus based on processing requests from a first terminal apparatus and a second terminal apparatus, wherein the second terminal apparatus is configured to acquire a right to control the control unit from the first terminal apparatus; and
a processing request management unit configured to manage a plurality of processing requests output from the second terminal apparatus,
wherein the control unit controls the medical image capturing apparatus based on a processing request output from the second terminal apparatus,
wherein, in a case where the control unit has controlled the medical image capturing apparatus based on the processing request output from the second terminal apparatus, the first terminal apparatus acquires the right to control the control unit from the second terminal apparatus, and
wherein, in a case where the plurality of processing requests is output from the second terminal apparatus, the processing request management unit manages the plurality of processing requests using a first-in-first-out structure.

14. A medical image capturing method for controlling a medical image capturing apparatus based on processing requests from a first terminal apparatus and a second terminal apparatus, the medical image capturing method comprising:
transferring a right to control a control unit configured to control the medical image capturing apparatus, from the first terminal apparatus to the second terminal apparatus;
controlling the medical image capturing apparatus based on a processing request from the second terminal apparatus; and
transferring the right to control the control unit from the second terminal apparatus to the first terminal apparatus in a case where the medical image capturing apparatus has been controlled based on the processing request from the second terminal apparatus,
wherein a plurality of processing requests is managed by using a first-in-first-out structure.

15. A non-transitory storage medium storing a program causing a computer to execute the steps of the medical image capturing method according to claim 14.

* * * * *